US010900956B2

(12) United States Patent
Teitell et al.

(10) Patent No.: US 10,900,956 B2
(45) Date of Patent: Jan. 26, 2021

(54) SELECTING AND ISOLATING DESIRABLE T LYMPHOCYTES BY CHANGE IN MASS RESPONSES

(71) Applicant: The Regents of The University of California, Oakland, CA (US)

(72) Inventors: Michael A. Teitell, Tarzana, CA (US); Thomas A. Zangle, Salt Lake City, UT (US); Owen N. Witte, Sherman Oaks, CA (US); Daina Burnes Linton, Marina del Rey, CA (US)

(73) Assignee: The Regents of the University of California, Oakland, CA (US)

( * ) Notice: Subject to any disclaimer, the term of this patent is extended or adjusted under 35 U.S.C. 154(b) by 392 days.

(21) Appl. No.: 14/890,578

(22) PCT Filed: May 23, 2014

(86) PCT No.: PCT/US2014/039418
§ 371 (c)(1),
(2) Date: Nov. 11, 2015

(87) PCT Pub. No.: WO2014/190303
PCT Pub. Date: Nov. 27, 2014

(65) Prior Publication Data
US 2016/0103118 A1 Apr. 14, 2016

Related U.S. Application Data

(60) Provisional application No. 61/827,378, filed on May 24, 2013.

(51) Int. Cl.
*C12N 5/00* (2006.01)
*G01N 33/50* (2006.01)
*G01B 9/02* (2006.01)
*G01B 11/06* (2006.01)
*G02B 21/14* (2006.01)

(52) U.S. Cl.
CPC ....... *G01N 33/505* (2013.01); *G01B 9/02015* (2013.01); *G01B 11/06* (2013.01); *G02B 21/14* (2013.01); *G01N 2333/70517* (2013.01)

(58) Field of Classification Search
None
See application file for complete search history.

(56) References Cited

U.S. PATENT DOCUMENTS

| 5,133,601 | A | 7/1992 | Cohen et al. |
| 5,471,303 | A | 11/1995 | Ai et al. |
| 6,377,721 | B1 | 4/2002 | Walt et al. |
| 6,449,048 | B1 | 9/2002 | Olszak |
| 6,858,184 | B2 | 2/2005 | Pelrine et al. |
| 7,610,074 | B2 | 10/2009 | Boppart et al. |
| 8,343,497 | B2* | 1/2013 | Shi .................. A61K 39/00 424/184.1 |
| 8,524,488 | B2 | 9/2013 | Gimzewski et al. |
| 8,599,383 | B2 | 12/2013 | Teitell et al. |
| 8,994,864 | B2* | 3/2015 | Yamamoto .......... H01L 27/1461 348/294 |
| 9,810,683 | B2 | 11/2017 | Gimzewski et al. |
| 9,873,870 | B2* | 1/2018 | Flechtner ........... G01N 33/5047 |
| 10,203,331 | B2 | 2/2019 | Reed et al. |
| 2002/0196450 | A1 | 12/2002 | Olszak et al. |
| 2003/0234936 | A1 | 12/2003 | Marron |
| 2004/0058458 | A1 | 3/2004 | Anker et al. |
| 2004/0066520 | A1 | 4/2004 | Marron |
| 2004/0210289 | A1 | 10/2004 | Wang et al. |
| 2004/0218189 | A1 | 11/2004 | Izatt et al. |
| 2004/0252310 | A1 | 12/2004 | De Lega et al. |
| 2004/0258759 | A1 | 12/2004 | Suslick et al. |
| 2005/0057756 | A1 | 3/2005 | Fang-Yen et al. |
| 2005/0058990 | A1 | 3/2005 | Guia et al. |
| 2005/0088663 | A1 | 4/2005 | De Groot et al. |
| 2005/0117165 | A1 | 6/2005 | Holbrook et al. |
| 2005/0122527 | A1 | 6/2005 | Boccara et al. |
| 2005/0167578 | A1 | 8/2005 | Riza et al. |
| 2005/0195405 | A1 | 9/2005 | Ina et al. |
| 2005/0200856 | A1 | 9/2005 | Groot |
| 2005/0225769 | A1 | 10/2005 | Bankhead et al. |
| 2005/0239047 | A1 | 10/2005 | Gimzewski et al. |

(Continued)

FOREIGN PATENT DOCUMENTS

| CN | 1415067 A | 4/2003 |
| CN | 101313196 A | 11/2008 |

(Continued)

OTHER PUBLICATIONS

Rosenberg et al ( 2008, Nat. Rev. Cancer, 8, 299-308).*
U.S. Office Action dated Oct. 7, 2011 issued in U.S. Appl. No. 12/436,702.
U.S. Office Action dated Jul. 20, 2012 issued in U.S. Appl. No. 12/436,702.
U.S. Final Office Action dated Jan. 22, 2013 issued in U.S. Appl. No. 12/436,702.

(Continued)

Primary Examiner — Michail A Belyavskyi
(74) Attorney, Agent, or Firm — Tom Hunter; Weaver Austin Villeneuve & Sampson LLP

(57) ABSTRACT

In certain embodiments methods of identifying T cell receptors that respond to specific target cell antigens are provided, where the methods comprise providing a substrate bearing a plurality of target cells (e.g., mammalian cells); contacting the target cells on the substrate with CD8+ T cells; and using label-free optical imaging to identify an increase in mass of a T-cell and/or a decrease in mass of a target cell, where an increase in mass of a T cell and/or a decrease in mass of a target cell is an indicator that said T cell bears a T cell receptor activated by antigens presented on said target cell.

20 Claims, 20 Drawing Sheets

(56) References Cited

U.S. PATENT DOCUMENTS

| | | |
|---|---|---|
| 2005/0248770 A1 | 11/2005 | Lin |
| 2006/0291712 A1 | 12/2006 | Popescu et al. |
| 2007/0279638 A1 | 12/2007 | Choo et al. |
| 2008/0018966 A1 | 1/2008 | Dubois et al. |
| 2009/0125242 A1 | 5/2009 | Choi et al. |
| 2009/0163564 A1 | 6/2009 | Borden et al. |
| 2009/0238817 A1 | 9/2009 | Kozlowski |
| 2009/0325211 A1 | 12/2009 | Fang et al. |
| 2010/0079763 A1 | 4/2010 | Arvidson et al. |
| 2010/0284016 A1 | 11/2010 | Teitell et al. |
| 2012/0107840 A1 | 5/2012 | Wagner et al. |
| 2014/0080171 A1 | 3/2014 | Gimzewski et al. |
| 2014/0178865 A1 | 6/2014 | Reed et al. |
| 2018/0156779 A1 | 6/2018 | Gimzewski et al. |

FOREIGN PATENT DOCUMENTS

| | | |
|---|---|---|
| CN | 101346673 A | 1/2009 |
| EP | 1971690 | 9/2008 |
| EP | 2224946 | 9/2010 |
| JP | 2007-524075 A | 8/2007 |
| JP | 2009-276327 A | 11/2009 |
| JP | 2010-505123 A | 2/2010 |
| JP | 2011-509248 A | 3/2011 |
| WO | WO 01/31286 A2 | 5/2001 |
| WO | WO 2005/001445 A2 | 1/2005 |
| WO | WO 2007/123579 A2 | 11/2007 |
| WO | WO 2008/060369 A2 | 5/2008 |
| WO | WO 2009/086516 A1 | 7/2009 |
| WO | WO 2013/019984 A1 | 2/2013 |
| WO | WO 2014/190303 A1 | 11/2014 |

OTHER PUBLICATIONS

U.S. Notice of Allowance dated Jul. 30, 2013 issued in U.S. Appl. No. 12/436,702.

PCT International Search Report and Written Opinion dated Sep. 25, 2014 issued in PCT/US2014/039418.

PCT International Preliminary Report on Patentability dated Dec. 3, 2015 issued in PCT/US2014/039418.

European Communication pursuant to Rules 161(2) and 162 EPC dated Jan. 13, 2016 issued in EP 14801181.0.

PCT International Search Report and Written Opinion dated Dec. 12, 2012 issued in PCT/US2012/049388.

PCT International Preliminary Report on Patentability dated Feb. 13, 2014 issued in PCT/US2012/049388.

Australian Patent Examination Report No. 1 dated Feb. 12, 2015 issued in AU 2012290024.

Chinese First Office Action dated Nov. 24, 2015 issued in CN 201280048126.5.

European Communication pursuant to Rules 161(2) and 162 EPC dated Mar. 12, 2014 issued in EP 12 819 806.6.

European Extended Search Report dated Mar. 16, 2015 issued in EP 12 819 806.6.

Balagopalan et al. (Jan. 2011) "Imaging techniques for assaying lymphocyte activation in action," *Nat Rev Immunol*, 11:21-33.

Barer, R. (Mar. 1, 1952) "Interference microscopy and mass determination," *Nature*, 169:366-367.

Davies et al. (Mar. 29, 1952) "Interference microscopy and mass determination," *Nature*, 169:541.

Davies et al. (Sep. 1954) "The Use of the Interference Microscope to Determine Dry Mass in Living Cells and as a Quantitative Cytochemical Method," *Quarterly Journal of Microscopical Science*, 95(part 3):271-304.

Edwards et al. (2011) "T cell recognition of weak ligands: roles of signaling, receptor number, and affinity," *Immunol Res*, 50(1):39-48 [NIH Public Access—Author Manuscript 17pp].

Erskine et al. (2012) "Determining Optimal Cytotoxic Activity of Human Her2neu Specific CD8 T cells by Comparing the Cr51 Release Assay to the xCELLigence System," *Journal of Visualized Experiments and ACEA Biosciences*, 66: e3 683 (1-6).

Gamble et al. (Jan. 7, 1960) "Studies in Histochemistry: LVIL. Determination of the Total Dry Mass of Human Erythrocyes by Interference Microscopy and X-ray Microradiography," *The Journal of Biophysics and Biochemical Cytology*, 8:53-60.

Gohring et al. (2010) "Label free detection of CD4+ and CD8+ T cells using the optofluidic ring resonator," *Sensors*, 10(6):5798-5808.

Kwong et al. (2009) "Modular nucleic acid assembled p/MHC microarrays for multiplexed sorting of antigen-specific T cells," *J Am Chem Soc*, 131(28):9695-9703.

Ma et al. (Jun. 2011) "A clinical microchip for evaluation of single immune cells reveals high functional heterogeneity in phenotypically similar T cells," *Nature Medicine*, 17(6):738-743.

Mir et al. (2011) "Optical measurement of cycle-dependent cell growth," *Proceedings of the National Academy of Sciences*, 108(32): 13124-13129.

Moore et al. (2004) "Tracking the Recruitment of Diabetogenic $CD8^+$T-Cells to the Pancreas in Real Time," *Diabetes*, 53:1459-1466.

Pittet et al. (2007) "In vivo imaging of T cell delivery to tumors after adoptive transfer therapy," *PNAS*, 104(30):12457-12461.

Reed et al. (2006) "Applications of Imaging Interferometry," *Proceedings of SPIE, The International Society for Optical Engineering*, 0277-786X, 6293:629301-1-629301-8.

Reed et al. (Aug. 14, 2006) "Observation of nanoscale dynamics in cantilever sensor arrays," *NANOTECHNOLOGY*, 17(15):3873-3879.

Reed et al. (Jun. 11, 2008) "High throughput cell nanomechanics with mechanical imaging interferometry," *NANOTECHNOLOGY*, 19(23):pp. 1-8.

Reed et al. (2008) "Live Cell Interferometry Reveals Cellular Dynamism During Force Propagation," *ACS NANO*, 2(5):841-846.

Reed et al. (Sep. 2011) "Rapid, massively parallel single-cell drug response measurements via live cell interferometry," *Biophysical Journal*, 101:1025-1031.

Stone et al. (2009) "T-cell receptor binding affinities and kinetics: impact on T-cell activity and specificity," *Immunology*, 126(2):165-176.

Tian et al. (2007) "$CD8^+$T cell activation is governed by TCR-peptide/MHC affinity, not dissociation rate," *Journal of Immunology*, 179:2952-2960.

Tzur et al. (2011) "Optimizing optical flow cytometry for cell volume-based sorting and analysis," *PLoS One*, 6(1):e16053 (1-9).

Whiteside, T.L. (2004) "Methods to monitor immune response and quality control," *Dev Biol (Basel)* 116:219-228; discussion 229-236 [Abstract available, 2 pages].

Wooldridge et al. (2009) "Tricks with tetramers: how to get the most from multimeric peptide-MHC," *Immunology*, 126:147-164.

Zangle et al. (Jul. 2013) "Quantifying Biomass Changes of Single CD8+ T Cells during Antigen Specific Cytotoxicity," *PLoS One* 8(7):e68916 (1-8).

U.S. Office Action dated Mar. 29, 2016 issued in U.S. Appl. No. 14/088,992.

U.S. Notice of Allowance dated Jan. 17, 2017 issued in U.S. Appl. No. 14/088,992.

U.S. Notice of Allowance dated May 18, 2017 issued in U.S. Appl. No. 14/088,992.

U.S. Notice of Allowance dated Sep. 11, 2017 issued in U.S. Appl. No. 14/088,992.

U.S. Restriction Requirement dated Jun. 6, 2016 issued in U.S. Appl. No. 14/235,547.

U.S. Office Action dated Nov. 18, 2016 issued in U.S. Appl. 14/235,547.

U.S. Final Office Action dated Aug. 24, 2017 issued in U.S. Appl. No. 14/235,547.

Canadian First Office Action dated Oct. 18, 2017 issued in CA 2,912,842.

Chinese First Office Action dated Jun. 30, 2017 issued in CN 201480029374.4.

Chinese Second Office Action [No translation] dated Mar. 13, 2018 issued in CN 201480029374.4.

European Extended Search Report dated Nov. 18, 2016 issued in EP 14801181.0.

(56) References Cited

OTHER PUBLICATIONS

Japanese Notice of Reasons for Rejection dated Nov. 20, 2017 issued in JP 2016-515128.
Korean Notice of Grounds for Rejection dated Mar. 15, 2018 issued in KR 10-2015-7033208.
Australian Patent Examination Report No. 1 dated Jun. 6, 2017 issued in AU 2016200629.
Chinese Second Office Action dated Jul. 25, 2016 issued in CN 201280048126.5.
Chinese Third Office Action dated Mar. 24, 2017 issued in CN 201280048126.5.
Japanese Office Action dated May 25, 2016 issued in JP 2014-524086.
Japanese Decision to Grant Patent dated Apr. 12, 2017 issued in JP 2014524086.
Burnes, D (2012) "Quantifying biomass changes of single cells during antigen-specific CD8+ T cell mediated cytotoxicity" *Electronic Thesis and Dissertations UCLA* 33 pages.
Hobeika et al. (Jan. 1, 2005) "Enumerating Antigen-Specific T-Cell Responses in Peripheral Blood," *Journal of Immunotherapy*, 28(1): 63-72.
Rathmell et al. (Sep. 1, 2000) "In the Absence of Extrinsic Signals, Nutrient Utilization by Lymphocytes is Insufficient to Maintain Either Cell Size or Viability," *Molecular Cell.*, 6(3): 683-692.
Zangle et al. (Feb. 19, 2014) "High-Throughput Screening of T Cell Cytotoxic Events by Biomass Profiling," *Biophysical Journal 4095—Pos Board B823*, 106(2):811a (1 page).
U.S. Notice of Allowance dated Sep. 20, 2018 issued in U.S. Appl. No. 14/235,547.
Extended European Search Report dated Jun. 19, 2018 issued in EP 18155863.6.
Japanese Notice of Allowance dated Jun. 4, 2018 issued in JP 2016-515128.
Canadian First Office Action dated Jun. 5, 2018 issued in CA 2,843,445.
European Office Action dated Jan. 15, 2019 issued in EP 12 819 806.6.
Japanese Decision to Grant Patent dated May 9, 2018 issued in JP 2017-094485.
Korean First Office Action dated Jul. 10, 2018 issued in KR 10-2014-7005381.
U.S. Office Action dated Jun. 25, 2019 issued in U.S. Appl. No. 15/726,285.
Australian Patent Examination Report No. 1 dated Jun. 7, 2019 issued in AU 2014268394.
Australian Patent Examination Report No. 1 dated Jun. 27, 2019 issued in AU 2018232924.
U.S. Final Office Action dated Feb. 4, 2020 issued in U.S. Appl. No. 15/726,285.
European 2nd Office Action dated Nov. 25, 2019 issued in EP 12 819 806.6.
Popescu et al. (2008) "Optical imaging of cell mass and growth dynamics," *Am J Physiol*, 295: C538-0544 DOI: 10.1152/AJPCELL.00121.2008.
Rappaz, Benjamin et al. (May/Jun. 2009) "Noninvasive characterization of the fission yeast cell cycle by monitoring dry mass with digital holographic microscopy", *Journal of Biomedical Opticss* 14(3): 034049(1-5) (5 pages), DOI:10.1117/1.3147385.
Z. El-Schish et al. (2010) "Digital holographic microscopy—innovative and nondestructive analysis of living cells", XP055643679, (8 pages), Retrieved from the Internet: URL: http://muep.mau.se/bitstream/handle/2043/11217/Article%20ElSchish%20et%20a1%202010%20final%20version .pdf?sequence=1&isAllowed=y.

* cited by examiner

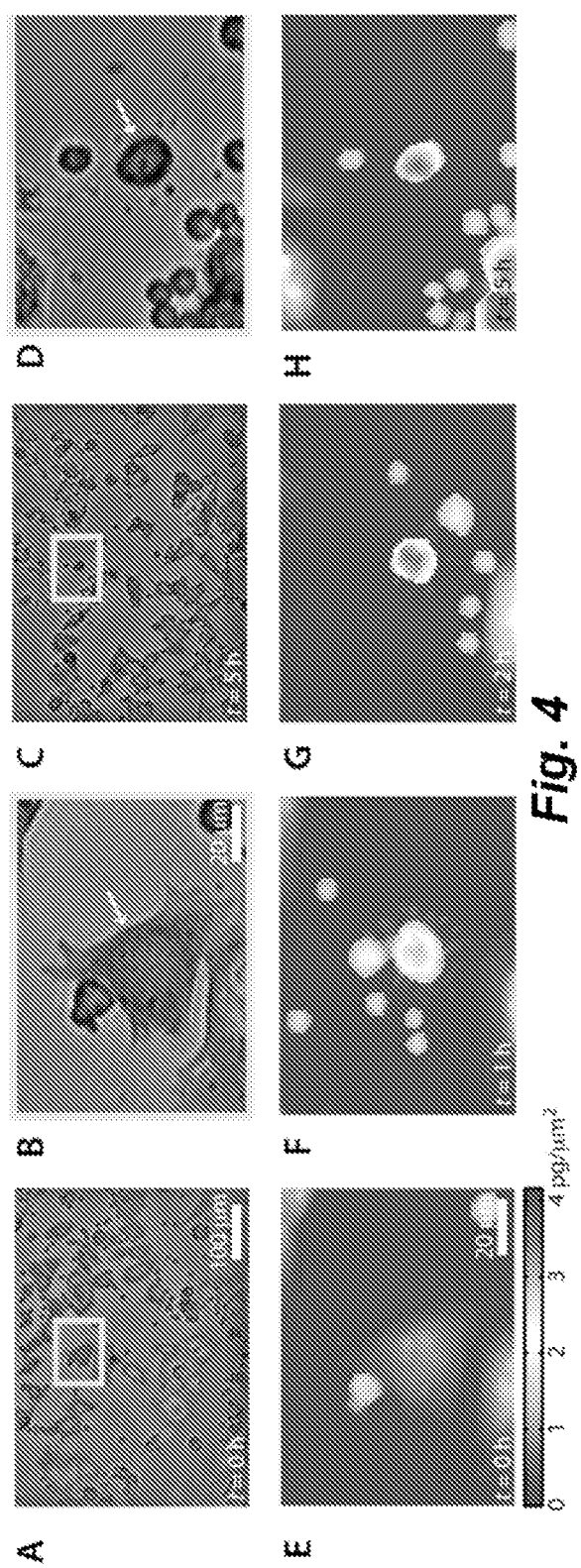

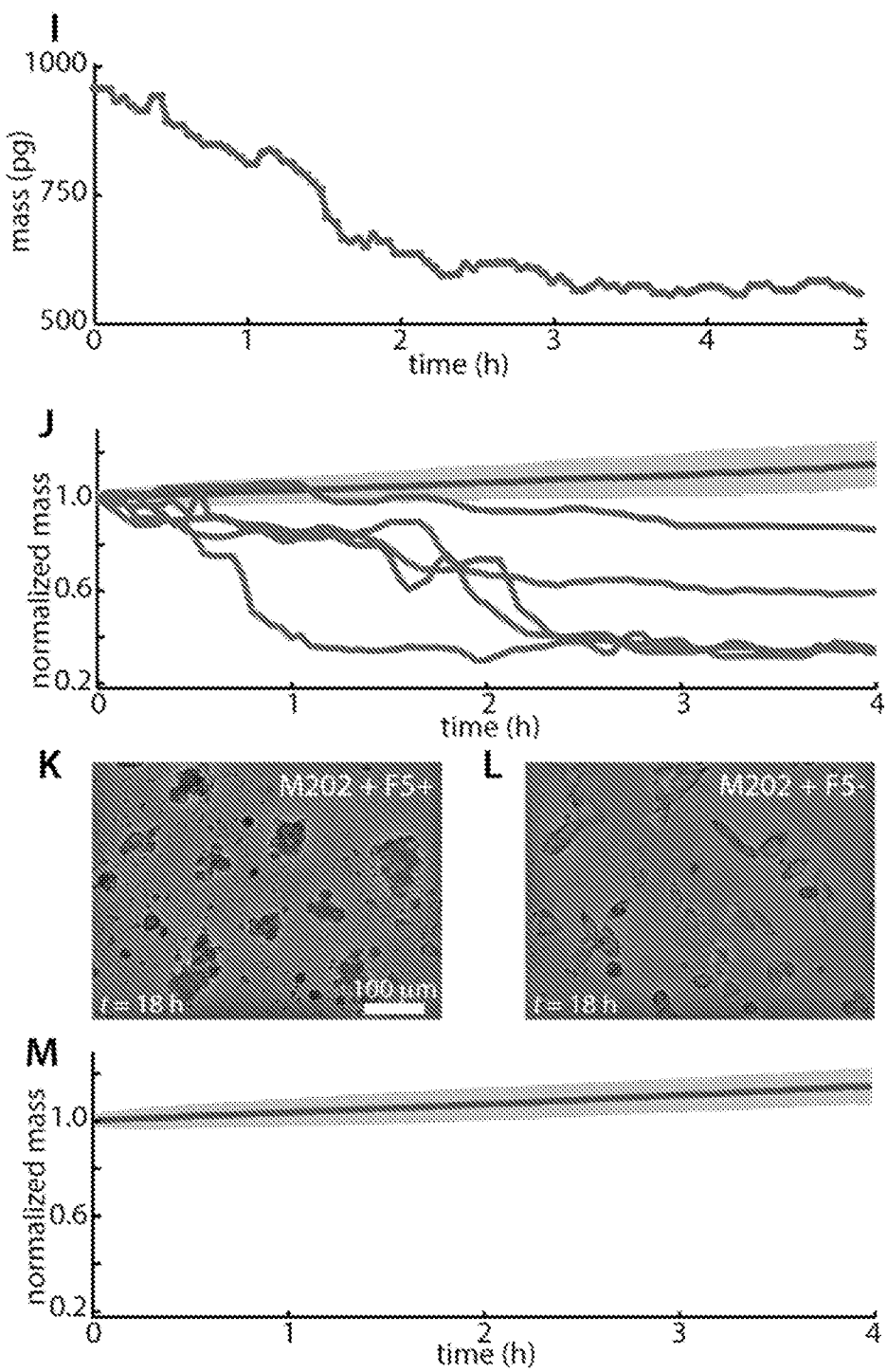
*Fig. 4, cont'd.*

SELECTING AND ISOLATING DESIRABLE T LYMPHOCYTES BY CHANGE IN MASS RESPONSES

CROSS-REFERENCE TO RELATED APPLICATIONS

This application is a U.S. 371 national phase of PCT/US2014/039418, filed on May 23, 2014, which claims benefit of and priority to U.S. Ser. No. 61/827,378, filed on May 24, 2013, both of which are incorporated herein by reference in their entirety for all purposes.

STATEMENT OF GOVERNMENTAL SUPPORT

This invention was made with Government support under CA009120 and CA157940 awarded by the National Institutes of Health. The Government has certain rights in the invention.

BACKGROUND

CD8+ T lymphocyte mediated cytotoxicity is an important component of the adaptive immune response against viruses and cancers, and is also implicated in autoimmunity (Kalinski et al. (2006) *Immunol Res.*, 36: 137-146; Tuma and Pamer (2002) *Curr. Opin. Immunol.* 14: 348-353). T cell mediated cytotoxicity is typically measured by target cell death or surrogate markers of effector cell cytotoxic capacity. The canonical assays are the $^{51}$Cr release assay and ELISPOT, both of which provide bulk measurements of whole lymphocyte population or sub-population responses (Hobeika et al. (2005) *J. Immunother.* 28: 63-72; Malyguine et al. (2007) *Adv. Exp. Med. Biol.* 601: 273-284). The introduction of peptide-MHC tetramers and microfluidic platforms has allowed for surrogate measures of cytotoxicity through analysis of T cell antigen specificity and cytokine secretion (Hobeika et al. (2005) *J. Immunother.* 28: 63-72; Kwong et al. (2009) *J. Am. Chem. Soc.* 131: 9695-9703; Ma et al. (2011) *Nat. Med.* 17: 738-743). Directly tracking T lymphocyte mediated cytotoxicity at the single cell level is advantageous for analyzing cytotoxic T cells (CTLs) within a mixed population, which is of particular relevance in assessing T cell recognition against cancer cells. Viable CTLs can potentially be cultured and expanded further, or the corresponding T cell receptors (TCRs) bearing optimal specificity toward immunogenic peptides can be molecularly cloned for utilization in a clinical setting (Rosenberg et al. (2008) *Nat. Rev. Cancer*, 8: 299-308).

Optical microscopy allows for direct identification and tracking of CTLs in the full context of target cell recognition and killing. Optical imaging methods such as epifluorescence, confocal microscopy, total internal reflection fluorescence and two photon laser scanning microscopy have been explored for the study of lymphocyte activation, but typically require antibody or conjugated protein labeling to track and quantify cells (Balagopalan et al. (2011) *Nat. Rev. Immunol.* 11: 21-33; Delon et al. (2002) *Immunol. Rev.* 189: 51-63). This limits applicability to studies of T lymphocytes due to transduction inefficiencies associated with diverse phenotypes as well as progressive differentiation towards exhaustion or senescence during in vitro culture, as is required for typical fluorescence labeling techniques (Sauce et al. (2002) *J. Hematother. Stem Cell Res.* 11: 929-940; Tran et al. (2008) *J. Immunother.* 31: 742-751).

SUMMARY

Methods are provided for identifying useful T lymphocytes that respond to specific target cell antigens by 1) increasing their mass through cellular activation; and/or 2) increasing their mass accumulation rate through activation; and/or 3) decreasing the target cell mass through killing the target cell. Changes in mass of the T cells and/or the target cells (bearing target antigens) are identified using label-free optical imaging techniques (e.g., LSI, lateral shearing interferometry, digital holographic microscopy, and the like).

Accordingly, in various aspects, the methods(s) contemplated herein may include, but need not be limited to, any one or more of the following embodiments:

Embodiment 1

A method of identifying T cell receptors that respond to specific target cell antigens, said method including: providing a substrate bearing a plurality of target cells; contacting said target cells on said substrate with CD8+ T cells; and using label-free optical imaging to identify an increase in mass of a T-cell and/or a decrease in mass of a target cell, where an increase in mass of a T cell and/or a decrease in mass of a target cell is an indicator that said T cell bears a T cell receptor activated by antigens presented on said target cell.

Embodiment 2

The method of embodiment 1, wherein an increase in mass of a T cell is detected and indicates that said T cell bears a T cell receptor activated by antigens presented on said target cell.

Embodiment 3

The method according to any one of embodiments 1-2, wherein a decrease in target cell mass indicates that the contacting T cell bears a T cell receptor activated by antigens presented on said target cell.

Embodiment 4

The method according to any one of embodiments 1-3, wherein death of target cells is monitored qualitatively using light microscopy.

Embodiment 5

The method according to any one of embodiments 1-4, further including selecting and/or isolating T cells that are activated.

Embodiment 6

The method according to any one of embodiments 1-5, further including selecting and culturing or storing T cells that are activated.

Embodiment 7

The method according to any one of embodiments 5-6, wherein said method includes selecting activated T cells using a micromanipulator.

Embodiment 8

The according to any one of embodiments 5-7, further including cloning T cell receptors from T cells that are selected.

Embodiment 9

The method according to any one of embodiments 1-8, wherein said target cells are in static media.

Embodiment 10

The method according to any one of embodiments 1-8, wherein said target cells are disposed in a microchannel.

Embodiment 11

The method according to any one of embodiments 1-8, wherein said target cells are disposed in microwells on a substrate.

Embodiment 12

The method of embodiment 11, wherein said substrate includes at least 10 microwells.

Embodiment 13

The method of embodiment 11, wherein said substrate includes at least 100 microwells.

Embodiment 14

The method of embodiment 11, wherein said substrate includes at least 1000 microwells.

Embodiment 15

The method according to any one of embodiments 11-14, wherein said T cell are introduced into said microwells.

Embodiment 16

The method of embodiment 15, wherein the microwells contain on average about 1 T cell per microwell.

Embodiment 17

The method according to any one of embodiments 11-16, wherein said microwells are fabricated from a polymer.

Embodiment 18

The method of embodiment 17, wherein said microwells are fabricated from a polymer with an index of refraction approximately equal to that of water (e.g., MY133, a UV-curable polymer from MY polymers).

Embodiment 19

The method of embodiment 17, wherein said microwells are fabricated from PDMS.

Embodiment 20

The method according to any one of embodiments 11-16, wherein said microwells are etched into a silicon substrate.

Embodiment 21

The method according to any one of embodiments 1-20, wherein said substrate is reflective.

Embodiment 22

The method according to any one of embodiments 1-21, wherein said using label-free optical imaging includes detecting a phase shift in light passing through said cell(s) caused by the change in T-cell mass and/or target cell mass.

Embodiment 23

The method of embodiment 22, wherein said label-free optical imaging includes quantitative phase imaging microscopy.

Embodiment 24

The method of embodiment 23, wherein said label-free optical imaging includes a method selected from the group consisting of live cell interferometry (LCI), digital holography, and lateral shearing interferometry.

Embodiment 25

The method of embodiment 24, wherein said label-free optical imaging includes live cell interferometry including: providing said substrate in an observation chamber of an interference microscope adapted to measure a fractional phase shift between a test beam of light and a reference beam of light; exposing the cell to a test beam of light at an illumination wavelength; measuring the fractional phase shift between the test beam of light propagating through the cell and the reference beam of light; and using said fractional phase shift or a parameter derived therefrom as a measure of the increase in mass of the T cell and/or the decrease in mass of the target cell.

Embodiment 26

The method of embodiment 25, wherein said fractional phase shift is integrated across substantially the entire projected area of the cell whose mass change is being determined.

Embodiment 27

The method of embodiment 25, wherein said measure of the increase in mass of the T cell and/or the decrease in mass of the target cell is calculated as parameter m: $m \propto \int \emptyset \lambda \, dA$ where $\emptyset$ is the measured fractional phase shift, $\lambda$ is the illumination wavelength, and integration is performed across entire cell area, A.

Embodiment 28

The method of embodiment 25, wherein said measure of the increase in mass of the T cell and/or the decrease in mass of the target cell is calculated as $m = k \int \varphi \lambda \, dA$ where m is cell dry mass, $\varphi \lambda$ is the measured phase shift, k is a mass conversion factor taken as 5.56 pg/µm$^3$, and A is projected area.

Embodiment 29

The method according to any one of embodiments 25-28, wherein the method is performed using a live cell interferometry system including: a detector operatively coupled to a microscope; a sample chamber (perfusion imaging chamber) containing said substrate including a plurality of microwells; and an interferometer including a beam splitter, a reference mirror, and a reference fluid chamber that compensates for the optical path length through the sample chamber.

Embodiment 30

The method of embodiment 29, wherein the sample chamber includes at least one perfusion conduit adapted to circulate a cell media within the chamber.

Embodiment 31

The method of embodiment 16, wherein the live cell interferometry system includes a processor element and a memory storage element adapted to process and store one or more images of cells.

Embodiment 32

The method of embodiment 24, wherein said label-free optical imaging includes lateral shearing interferometry using a quadriwave lateral shearing interferometer mounted on a transmission white-light microscope.

Embodiment 33

The method according to any one of embodiments 1-32, wherein the mass of the cell(s) is observed a plurality of times so as to observe how the mass of the cell(s) changes over a period of time.

Embodiment 34

The method according to any one of embodiments 1-33, wherein the method is used to quantify masses of a plurality of cells.

Embodiment 35

The method according to any one of embodiments 1-34, wherein the method is used to quantify masses of at least 1,000 different cells.

Embodiment 36

The method according to any one of embodiments 1-34, wherein the method is used to quantify masses of at least 10,000 different cells.

Embodiment 37

The method according to any one of embodiments 1-36, wherein said target cells comprise cancer cells.

Embodiment 38

The method of embodiment 37, wherein said target cells comprise cells of a cancer selected from the group consisting of acute lymphoblastic leukemia (ALL), acute myeloid leukemia (AML), Adrenocortical carcinoma, AIDS-related cancers (e.g., kaposi sarcoma, lymphoma), anal cancer, appendix cancer, astrocytomas, atypical teratoid/rhabdoid tumor, bile duct cancer, extrahepatic cancer, bladder cancer, bone cancer (e.g., Ewing sarcoma, osteosarcoma, malignant fibrous histiocytoma), brain stem glioma, brain tumors (e.g., astrocytomas, brain and spinal cord tumors, brain stem glioma, central nervous system atypical teratoid/rhabdoid tumor, central nervous system embryonal tumors, central nervous system germ cell tumors, craniopharyngioma, ependymoma, breast cancer, bronchial tumors, burkitt lymphoma, carcinoid tumors (e.g., childhood, gastrointestinal), cardiac tumors, cervical cancer, chordoma, chronic lymphocytic leukemia (CLL), chronic myelogenous leukemia (CML), chronic myeloproliferative disorders, colon cancer, colorectal cancer, craniopharyngioma, cutaneous t-cell lymphoma, duct cancers e.g. (bile, extrahepatic), ductal carcinoma in situ (DCIS), embryonal tumors, endometrial cancer, ependymoma, esophageal cancer, esthesioneuroblastoma, extracranial germ cell tumor, extragonadal germ cell tumor, extrahepatic bile duct cancer, eye cancer (e.g., intraocular melanoma, retinoblastoma), fibrous histiocytoma of bone, malignant, and osteosarcoma, gallbladder cancer, gastric (stomach) cancer, gastrointestinal carcinoid tumor, gastrointestinal stromal tumors (GIST), germ cell tumors (e.g., ovarian cancer, testicular cancer, extracranial cancers, extragonadal cancers, central nervous system), gestational trophoblastic tumor, brain stem cancer, hairy cell leukemia, head and neck cancer, heart cancer, hepatocellular (liver) cancer, histiocytosis, langerhans cell cancer, Hodgkin lymphoma, hypopharyngeal cancer, intraocular melanoma, islet cell tumors, pancreatic neuroendocrine tumors, kaposi sarcoma, kidney cancer (e.g., renal cell, Wilm's tumor, and other kidney tumors), langerhans cell histiocytosis, laryngeal cancer, leukemia, acute lymphoblastic (ALL), acute myeloid (AML), chronic lymphocytic (CLL), chronic myelogenous (CML), hairy cell, lip and oral cavity cancer, liver cancer (primary), lobular carcinoma in situ (LCIS), lung cancer (e.g., childhood, non-small cell, small cell), lymphoma (e.g., AIDS-related, Burkitt (e.g., non-Hodgkin lymphoma), cutaneous T-Cell (e.g., mycosis fungoides, Sézary syndrome), Hodgkin, non-Hodgkin, primary central nervous system (CNS)), macroglobulinemia, Waldenström, male breast cancer, malignant fibrous histiocytoma of bone and osteosarcoma, melanoma (e.g., childhood, intraocular (eye)), merkel cell carcinoma, mesothelioma, metastatic squamous neck cancer, midline tract carcinoma, mouth cancer, multiple endocrine neoplasia syndromes, multiple myeloma/plasma cell neoplasm, mycosis fungoides, myelodysplastic syndromes, Myelogenous Leukemia, Chronic (CML), multiple myeloma, nasal cavity and paranasal sinus cancer, nasopharyngeal cancer, neuroblastoma, oral cavity cancer, lip and oropharyngeal cancer, osteosarcoma, ovarian cancer, pancreatic cancer, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pituitary tumor, plasma cell neoplasm, pleuropulmonary blastoma, primary central nervous system (CNS) lymphoma, prostate cancer, rectal cancer, renal cell (kidney) cancer, renal pelvis and ureter, transitional cell cancer, rhabdomyosarcoma, salivary gland cancer, sarcoma (e.g., Ewing, Kaposi, osteosarcoma, rhadomyosarcoma, soft tissue, uterine), Sézary syndrome, skin cancer (e.g., melanoma, merkel cell carcinoma, basal cell carcinoma, nonmelanoma), small intestine cancer, squamous cell carcinoma, squamous neck cancer with occult primary, stomach (gastric) cancer, testicular cancer, throat cancer, thymoma and thymic carcinoma, thyroid cancer, trophoblastic tumor, ureter and renal pelvis cancer, urethral cancer, uterine cancer, endometrial cancer, uterine sarcoma, vaginal cancer, vulvar cancer, Waldenström macroglobulinemia, and Wilm's tumor.

Embodiment 39

The method of embodiment 37, wherein said target cells comprise cells of a cancer selected from the group consisting of breast cancer, central nervous system cancer, cervical cancer, colorectal cancer, testicular cancer, ovarian cancer, leukemia, a lymphoma, a melanoma, a soft tissue sarcoma, testicular cancer, and thyroid cancer.

Embodiment 40

The method of embodiment 37, wherein said target cells comprise cancer stem cells.

Embodiment 41

The method of embodiment 37, wherein said target cells comprise metastatic cells.

Embodiment 42

The method according to any one of embodiments 1-36, wherein said target cells comprise cells infected with a pathogen.

Embodiment 43

The method of embodiment 42, wherein said target cells comprise cells infected with a pathogen selected from the group consisting of a bacterium, a fungus, and a virus.

Embodiment 44

The method according to any one of embodiments 1-36, wherein said target cells comprise recombinant cells transfected with a construct that expresses a heterologous protein or peptide.

BRIEF DESCRIPTION OF THE DRAWINGS

FIG. 2A: Workflow for T cell mass measurement experiments. Donor peripheral blood mononuclear cells (PBMCs) are transduced with the MART1 specific, F5 TCR and enriched for CD8+ T cells. A subset of these T cells are analyzed by flow cytometry to confirm a transduction efficiency of greater than 50%. The remaining cells are imaged on the LCI with MART1 expressing, HLA-matched (or mismatched control) M202 target cells. FIG. 2B: Sample LCI data showing the phase shift and mass distributions in an activated, F5-transduced CD8+ T cell, several unresponsive T cells, and a dying target cell.

FIG. 4, panels A-M, illustrate LCI tracking of target cell death during T cell mediated cytotoxicity. Panels A-H: Images of a single cytotoxic event occurring immediately after the start of imaging (t=0 is approximately 30 min after plating CTLs onto target cells). Panels A-D: intensity images at t=0 and 5 h of imaging demonstrating CTL mediated target cell killing. Boxes in panel A and panel C, indicate the subregion in images panel B and panel D. Arrows in panel B and panel D indicate the target cell tracked by mass profiling in (panels E-I). Panel E: LCI mass profile of selected target cell after initiation of persistent contact with a target cell at the start of imaging. Panels F-H: LCI mass profile of dying target cell. Panel I: Measured total mass vs. time for target cell shown in panels E-H. Panel J: Normalized mass of killed vs. healthy target cells over time. Normalized mass is mass divided by initial mass. Healthy cells show roughly 15% increase in normalized mass over 4 h (blue line indicates mean of n=311 healthy M202 cells, grey region indicates +/−SD). Killed target cells (red lines) show a decrease in mass of 20 to 60% over 1-4 h. Panel K: intensity image of stage location shown in panel A and panel C after 18 h of imaging, showing nearly complete death of target cells. Panel L: Intensity image of stage after 18 h of imaging M202 cells plated with untransduced (F5−) CD8+ T cells showing viability of target cells plated with nonspecific T cells. Panel M: Normalized mass vs. time for n=2058 healthy M202 cells treated with untransduced, control CTLs, showing roughly 15% increase in mass over 4 h.

FIG. 6A: time 0; FIG. 6B: time 1 hr; FIG. 6C: time 2 hr; FIG. 6D: time 3 hr; FIG. 6E: time 4 hr; FIG. 6F: time 5 hr.

DETAILED DESCRIPTION

Figure 1:
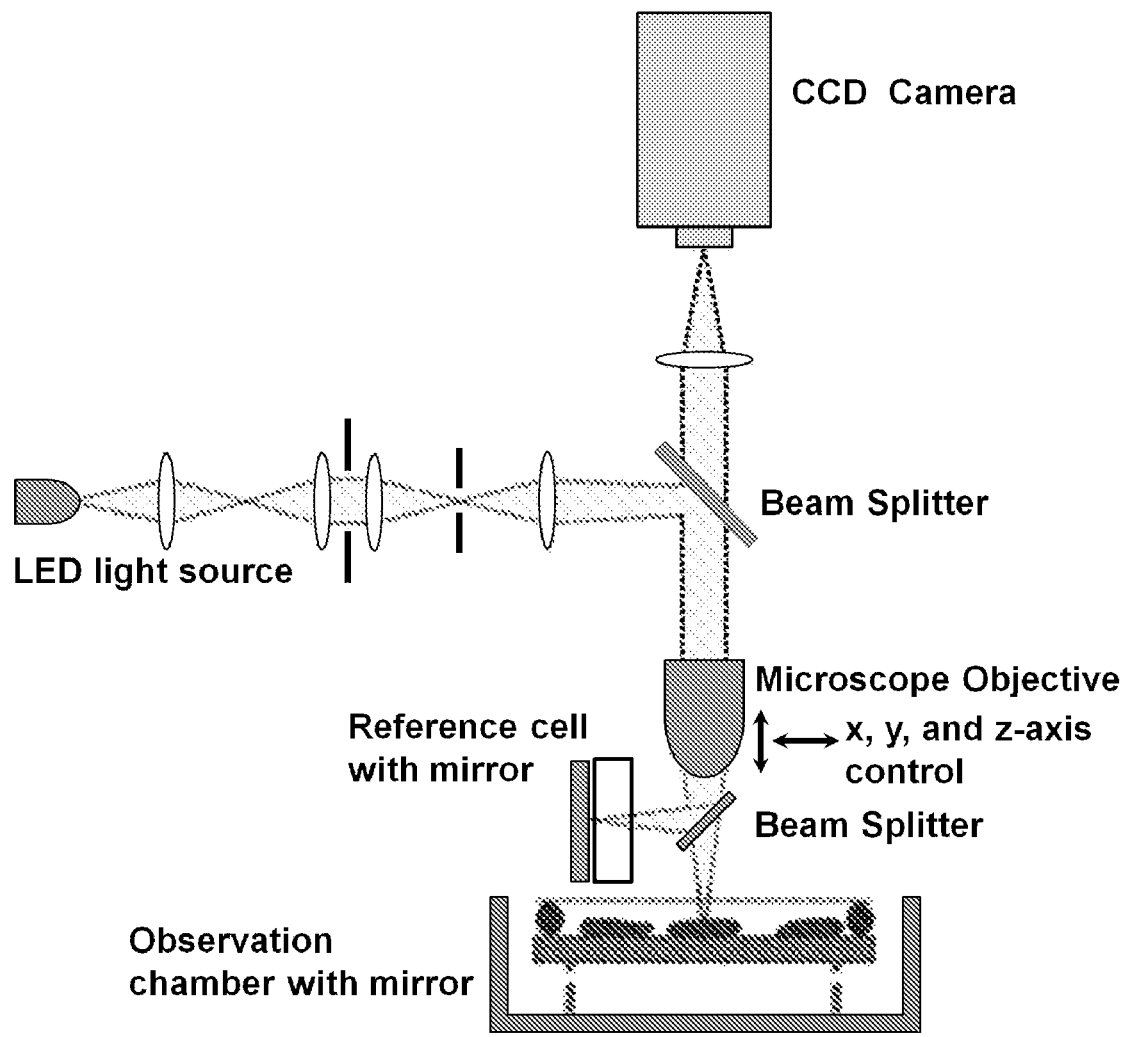
FIG. 1 schematically illustrates one embodiment of a live cell interferometer (LCI). In this illustrative, but non-limiting embodiment, the LCI comprises a Michelson-type interference microscope that compares the optical thickness of a reference cell to the optical thickness of samples placed in the observation chamber. Suspended in the observation chamber is a mirrored substrate, allowing the LCI to make measurements of optical thickness on transparent cells. The relative position of the microscope objective and observation chamber can be controlled by computer and can be translatable in three-dimensions allowing for rapid, automated image acquisition. The live cell interferometer is capable of measuring the mass of both adherent and non-adherent cells.

The identification of T cell receptors (TCRs) against known or unknown antigens is a major bottleneck in the development of cancer immune therapies for a variety of reasons, including the low frequency of TCRs directed against self-antigens, the low affinity of desired TCRs, and the small amount of tissue available per patient. Existing approaches to measure T cell responses rely on bulk or surrogate assays, do not directly determine the effectiveness of T cell mediated cytotoxicity, and are inefficient and error prone for the isolation of these rare T cells.

Improved methods for the identification, isolation, and characterization of desirable T lymphocytes with specificity towards desired antigens are described herein. In various embodiments, the methods utilize label-free optical imaging to identify changes in mass of cells (e.g., an increase in mass of a T-cell and/or a decrease in mass of a target cell) as an indicator of T cell activation when T cells are presented with target cells bearing a cognate antigen.

In various embodiments, a substrate is provided on which are disposed a plurality of target cells (e.g., cancer cells, cells infected with a pathogen, cells expressing a characteristic marker, cells transfected with a construct to recombinatnly express a protein or peptide, etc.). The target cells are contacted with ctytotoxic T lymphocytes (CTLs) and those CTLs bearding a T cell receptor that recognizes/is activated by an antigen presented by the target cell(s) increase their mass. As the target cell is killed that cell shows a decrease in mass. Thus, an increase in mass of a T cell and/or a decrease in mass of a target cell is an indicator that the T cell bears a T cell receptor activated by antigens presented on the target cell.

By tracking T and target cell mass changes using label-free optical imaging methods, e.g., as described herein, the methods permit direct measurements of the target and responding T cell during T cell mediated cytotoxicity to facilitate TCR cloning for use in adoptive immunotherapy against cancer. These methods can similarly be used to identify T-cells that are activated by cells infected with pathogens (e.g., cells infected with virus, bacteria, fungus, etc.), to identify cells that express (e.g., recombinantly express) particular peptides or proteins, and the like.

More specifically, in various embodiments, the methods described herein can be exploited to identify useful T lymphocytes that respond to specific target cell antigens by 1) increasing their mass through cellular activation; and/or 2) increasing their mass accumulation rate through activation; and/or 3) decreasing the target cell mass through killing the target cell. This is an improvement over existing art in that it directly quantifies the response of cytotoxic T lymphocytes in a complex population at the single cell level.

In various embodiments, the change in cell mass is determined using various interferometric and/or quantitative phase imaging microscopy techniques. Illustrative, but non-limiting imaging methods include, but are not limited to, live cell interferometry (LCI), digital holography, and lateral shearing interferometry. However, many microscopy systems and methods can be adapted for use with the methods described herein. Accordingly certain embodiments can use scanning optical microscopes, confocal microscopes and the like. An illustrative and non-limiting list of publications that describe optical profiling methods and materials that can be adapted for use with the methods described herein include, but are not limited to U.S. Patent Application Nos: 2010/0284016; 2005/0248770; 2005/0225769; 2005/0200856; 2005/0195405; 2005/0122527; 2005/0088663; 2004/0252310; 2005/0117165; 2003/0234936; 2004/0066520; 2008/0018966, 2005/0167578, and the like.

Figure 12:
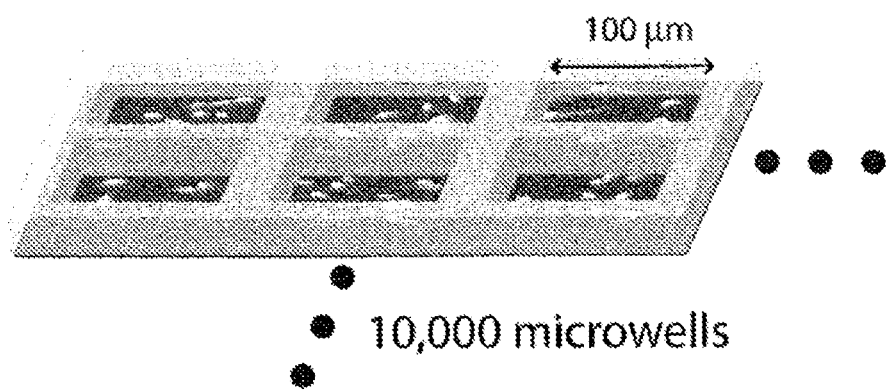
FIG. 12 shows a schematic illustration of a plurality of microwells on a substrate for use in isolating T cells.

Live cell interferometry (or another quantatitive phase imaging technique, including digital holographic microscopy, a lateral shearing interferometric camera connected to a ordinary microscope with live cell imaging capability, and the like) can be used to optically profile the mass response of a co-culture of target cells and candidate CTLs. In certain embodiments, screening is performed on target cells disposed on a substrate. In certain embodiments, screening can be performed on array of microwells (e.g., arrays comprising greater than 100, or greater than 1000, or greater than 10,000 microwells) fabricated by etching into a substrate or formation in a polymer (e.g., PDMS, a polymer with an index of refraction approximately equal to that of water such as MY133, a UV-curable polymer from MY polymers, and the like). in certain embodiments screening is performed on an array of approximately 1,000 or 5,000, or 10,000 to 15,000, or 20,000, or 25,000 microwells microfabricated in PDMS or MY133 (see, e.g., FIG. 12).

In certain embodiments for LCI, the target cells (or the microwells containing the target cells) are disposed on a reflective substrate (e.g., a reflective silicon substrate). Target cells can be grown on this substrate and/or in the microwells. Then T cells (e.g., CD8+ T cells) can be added (e.g., seeded onto the device at a density of approximately one CD8+ cell per well).

The microwell structure allows for the perfusion of media over the cells without allowing the T cells to float out of the microscope field of view. in certain embodiments, as indicated above, the microwells can be omitted particularly where the cells are grown in static media.

In certain embodiments the screen for target cells can comprise one or more of the following three steps to reduce false positives which would place an unnecessary burden on the TCR cloning efforts:

1. Monitor for death of target cells qualitatively using microscope intensity images; and/or
2. Check mass decrease kinetics of target cell to confirm that it is consistent with a cytotoxic event; and/or
3. Check mass increase kinetics of the activated T-cell to confirm that its behavior is consistent with that of an activated T-cell.

In certain embodiments target CTLS identified by this screening method can be removed from the microwells, e.g., using a micromanipulator, and stored for TCR cloning or downstream analysis, and/or can be recorded in a database. Live Cell Interferometry.

In certain embodiments changes in mass of the T cell(s) and/or target cell(s) are detected using live cell interferometry (LCI). Live cell interferometry (LCI) is a label-free, quantatitive phase microscopy technique that quantifies whole cell mass response within several hours and is uniquely suited to working with patient samples to identify TCRs against known or unknown antigens. Briefly, the interaction of light with matter slows light as it passes through a cell, resulting in a measurable shift in phase. By quantifying this phase shift across the entire cell, the mass of the cell can be determined very precisely. It has been shown that LCI can be used to profile the mass response or mass accumulation rate of hundreds or thousands of cells simultaneously under controlled culture conditions (see, e.g., PCT Publication No: WO2013019984 A1 (PCT/US2012/049388)). Here, we use the LCI as a platform to interrogate thousands of target cells as they are acted upon by candidate cytotoxic T cells (CTLs). As shown in FIGS. 2-5, the sensitivity of the LCI enables identification of CTLs on the basis of their effect on the mass of the target cell (target cell mass decrease as it dies) and the mass of the CTL itself during activation (mass increase). The high-throughput nature of LCI enables the identification of individual CTLs as targets for TCR cloning.

This approach illuminates fundamentals of T cell mediated cytotoxicity, including the kinetics and variability of T cell mass accumulation during the T cell response and the kinetics and variability of the target cell mass decrease due to T cell mediated cytotoxicity.

This approach also provides a generalized platform to directly identify CTLs without the use of surrogate assays. By directly measuring the mass response of lymphocytes during activation, the system provides a platform to broadly identify and select lymphocytes of interest based on key biophysical parameters such as mass increase during activation.

Live cell interferometry (LCI) is a label-free optical microscopy technique that measures whole cell responses. In certain embodiments LCI uses a Michelson-type interferometer to compare the optical thickness of living cells in a sample chamber to the optical thickness of fluid in a reference chamber and also quantifies the optical thickness difference between a cell and its surrounding media (Reed et al. (2011) *Biophys. J.* 101: 1025-1031; Reed et al. (2008) *ACS Nano*, 2: 841-846) (see, e.g., FIG. 1). The optical thickness difference due to the interaction of light with cellular biomass is linearly proportional to the material density of a cell (Ross (1967) *Phase contrast and interference microscopy for cell biologists*. London: Edward Arnold. xxi, 238 pp.). Based on this interaction, cell mass can be related to the measured phase retardation of light passing through each cell with 2% precision in total cell mass (Reed et al. (2011) *Biophys. J.* 101: 1025-1031; Reed et al. (2008) *ACS Nano*, 2: 841-846; Ross (1967) *Phase contrast and interference microscopy for cell biologists*. London: Edward Arnold. xxi, 238 pp.). Practically, LCI yields measurements of mass and mass accumulation or loss rates of 100-400 cells simultaneously per imaging location within 1-5 h of imaging (Reed et al. (2011) *Biophys. J.* 101: 1025-1031). With automated measurements every 2-5 minutes to allow for accurate tracking and mass determination during cytotoxic events at 20-50 imaging locations, this technique can quantify the mass of 2,000 to 20,000 cells.

Figure 2A:
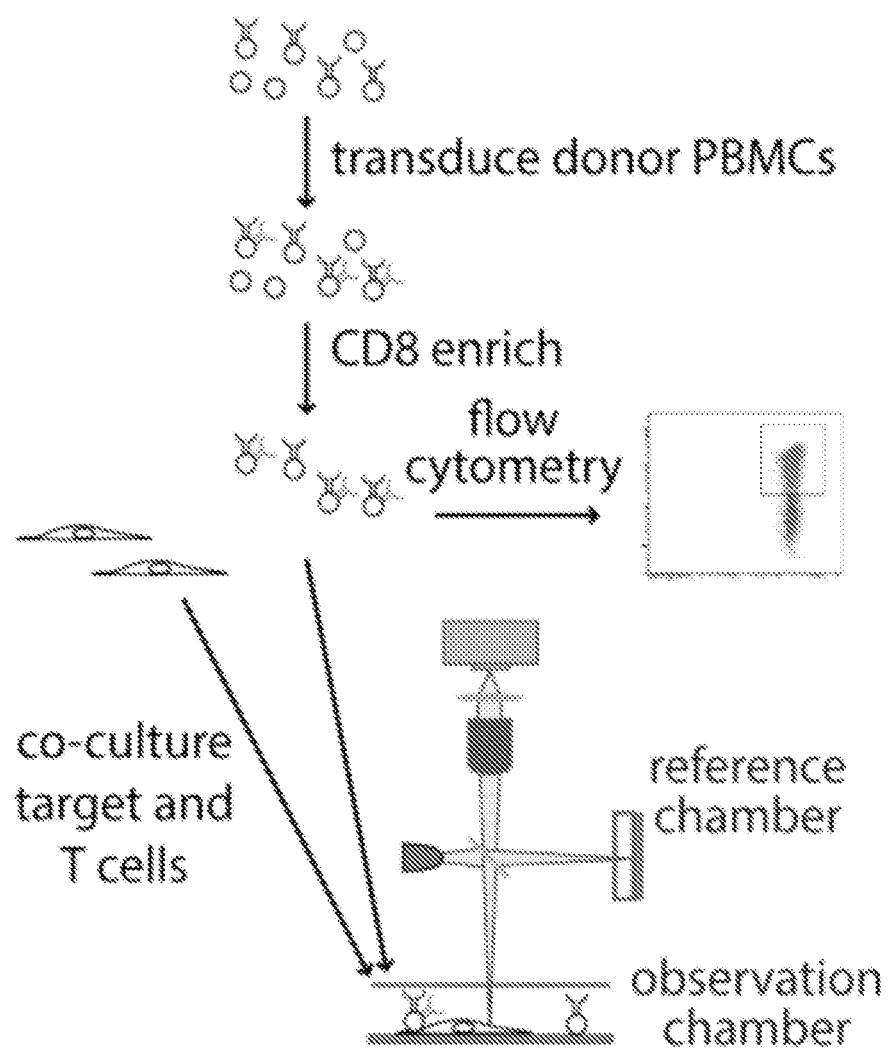
FIGS. 2A and 2B illustrate LCI measures mass of T and target cells.
Figure 2B:
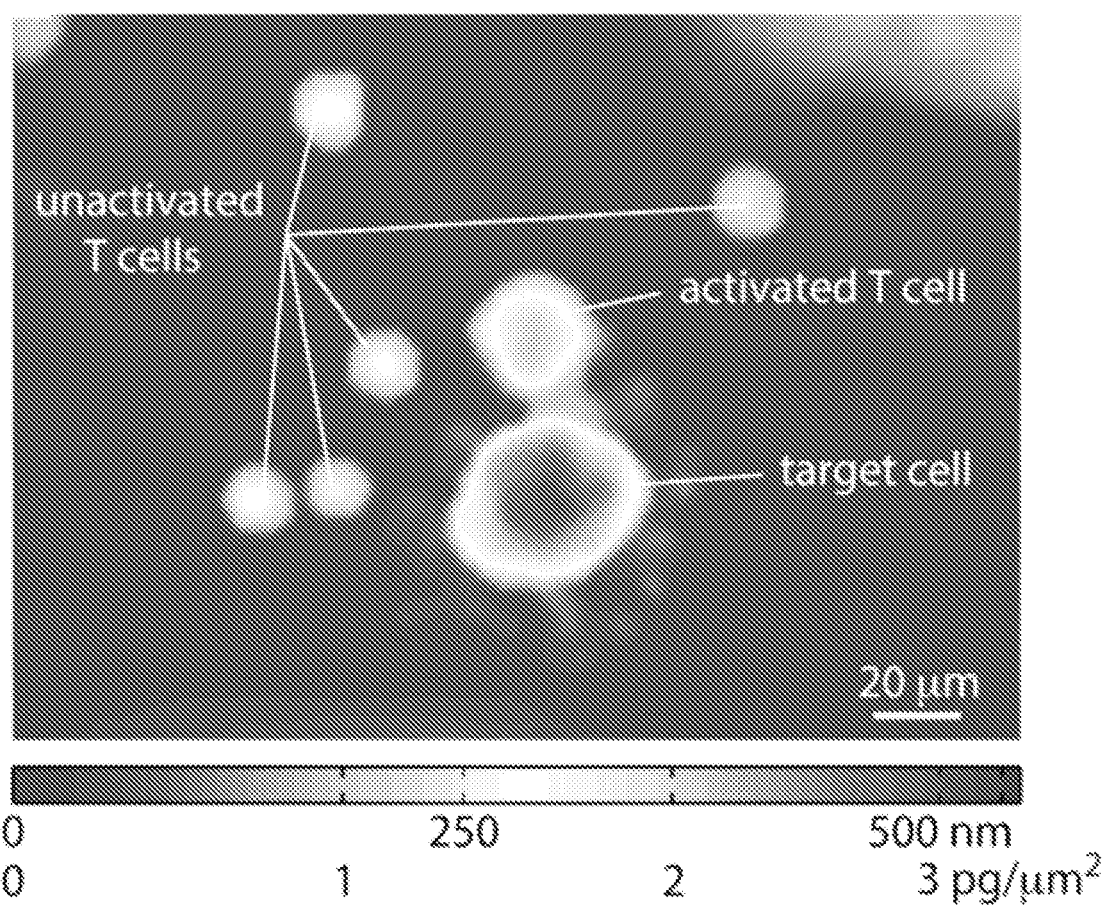

As illustrated in the Examples, in LCI, following image collection, the light phase shift data can corrected for phase wrapping errors that are caused by the integer wavelength ambiguity inherent in quantitative phase imaging (Ghiglia and Pritt, (1998) *Two-Dimensional Phase Unwrapping: Theory, Algorithms, and Software*: John Wiley & Sons.). The result is a map of phase shifts across each cell that can be converted into a map of local dry mass density (FIG. 2B). The total dry mass of a cell can be quantified as the sum of the local densities (Reed et al. (2011) *Biophys. J.* 101: 1025-1031; Ross (1967) *Phase contrast and interference microscopy for cell biologists*. London: Edward Arnold. xxi, 238 pp.; Mir et al. (2011) *Proc. Natl. Acad. Sci. USA*, 108: 13124-13129):

$$m = k \int \varphi \lambda \, dA, \qquad (1)$$

where m is cell dry mass, $\varphi\lambda$ is the measured phase shift, k is the mass conversion factor, and A is projected area. In certain embodiments the mass conversion factor (Barer (1952) *Nature* 169: 366-367; Mir et al. (2011) *Proc. Natl. Acad. Sci. USA*, 108: 13124-13129), which is a measure of the change in density per unit change in refractive index ($\Delta\rho/\Delta n$), can taken as $k = 5.56$ pg/$\mu m^3$ (Ross (1967) *Phase contrast and interference microscopy for cell biologists*. London: Edward Arnold. xxi, 238 pp.). This parameter, k, can be measured as a change in refractive index relative to the refractive index of water, therefore, the cell mass measured in this manner is the cell dry mass, or the mass of everything within the cell other than water.

It will be recognized, however, that the mass (m) of the cells need not be calculated. Simply a detection of the change in mass can provide a sufficient readout for the methods described herein. In certain embodiments, this can be provided simply by a measure of the phase shift, the phase shift integrated over the projected area of the cell (A), or as one more parameters derived from any of these measurements.

The approaches described herein directly track T lymphocyte mediated cytotoxicity at the single cell level without labeling by quantifying the mass of individual CTLs and their cognate target cells. Single cytotoxic events are identified and evaluated over time within a mixed population, using the mass data to confirm individual T cell mediated cytotoxicity events. As a proof of concept, we demonstrate tracking of up to 2,000 individual CTLs with specificity toward Melanocytic Antigen Recognized by T lymphocytes (MART1) responding against human leukocyte antigen (HLA) matched MART1+ target cells (Johnson et al. (2006) *J. Immunol.* 177: 6548-6559) (see, Example 1). Target cells are imaged by the LCI to establish a base-line mass accumulation rate. CTLs are then plated onto the target cells and individual cytotoxic events are identified as a characteristic decrease in target cell mass following contact with a corresponding T cell.

It is well established that T cells increase in size during activation (Rathmell et al. (2000) *Mol. Cell,* 6: 683-692). This previously observed increase in size may result from a change in solute concentration or osmolality within the cell as opposed to an increase in biomass (Tzur et al. (2011) *PLoS One,* 6: e16053). Until now this ambiguity has not been resolved but this result provides valuable insight into the mechanism of activation of a single CTL. Using the approach described herein, it was determined that the size increase in CTLs responding to cognate target cells is due to an increase in biomass and that biomass measurements provide robust identification of activated T cells. The capacity to measure the mass of a single CTL opens several potential downstream applications including T cell biological studies pertaining to metabolic or differentiation states in addition to the analysis of CTLs for potential use in adoptive immunotherapy protocols.

In typical embodiments, the LCI method can be performed using a live cell interferometry system that comprises a detector operatively coupled to the microscope, a sample assembly comprising an observation chamber adapted to contain the cell, a reference assembly comprising a reference chamber adapted to contain the reference cell, and a beam splitter for splitting a light beam from a light source into a test beam and a reference beam. In certain embodiments, the observation chamber comprises at least one perfusion conduit adapted to circulate a cell media within the chamber. In some embodiments the live cell interferometry system comprises a processor element and a memory storage element adapted to process and store one or more images of the cell. In embodiments, the mass of one or more cells is determined at a plurality of times so as to observe how the mass cells changes over a period of time and, optionally provide kinetics for such changes. Optionally, for example, changes in the mass property of the cell are observed over time to observe a temporal mass profile (e.g. the specific way in which the cell's mass changes over a period of time). Certain embodiments of the include the steps of comparing an observed temporal mass profile to a database of temporal mass profiles, wherein the database of temporal mass profiles is selected to include temporal mass profiles that are characteristic of T cell activation and/or target cell killing.

Lateral Shearing Interferometry.

In certain embodiments the change in cell size (e.g., the optical phase shift introduced by changes in cell size) can be determined using lateral shearing interferometry. Lateral shearing interferometry is a technique used to measure the phase gradients in one direction. The incident wave front is replicated into two identical but tilted wave fronts. After propagation, their mutual interference pattern is recorded, e.g., with a CCD camera. The phase gradients are recovered from the fringe deformation, by means of a Fourier deconvolution around the interferogram fringe frequency.

Multiwave interferometry (Primot and Sogno (1995) *J. Opt. Soc. Am. A,* 12(12): 2679) extends this principle to more than one gradient direction. In quadriwave lateral shearing interferometry (QWLSI) four replicas are created by a specific 2D diffraction grating. In this case, two gradients along two perpendicular directions are measured and then integrated to determine the field intensity and phase (Primot and Guérineau (2000) *Appl. Opt.* 39(31), 5715-5720). The interferogram deformation can be interpreted using either the wave or geometrical optics. Methods of using quadriwave lateral shearing interferometry for quantitative phase microscopy of living cells are described by Bon et al. (2009) *Optics Express* 17(15): 13080-13094). In addition, devices to implement QWLSI on a conventional microscope are commercially available (see, e.g., the SID4bio® from Phasics S.A., Marseille, France).

Digital Holographic Microscopy

Digital holographic microscopy provides quantitative measurement of the optical path length distribution that allows living cells to be described with a diffraction-limited transverse resolution and a sub-wavelength axial accuracy (see, e.g., Marquet et al. (2005) *Opt. Lett.* 30(5): 468-470). Digital holographic microscopy, as a quantitative phase-contrast imaging method, is a kind of optical interferometry that detects phase delay related to the light passing through the tested object. When passing through a relatively transparent sample, the intensity of the light changes very little, while the light through the sample speeds up or slows down and brings a corresponding phase change. The phase delay or advance depends on the relation of the refraction index between the sample and surrounding environment. Since the phase information is proportional to the optical path length (optical thickness) a depth profile and/or size/mass of sample can be calculated. Therefore, digital holography is particularly suitable to measure the phase object such as the living cells and microoptical elements.

In DHM, light wave front information originating from the object is digitally recorded as a hologram, from which a computer calculates the object image by using a numerical reconstruction algorithm.

To create the interference pattern, i.e., the hologram, in DHM, the cell(s) are illuminated using a a coherent (monochromatic) light source, e.g., a laser. The laser light is split into an object beam and a reference beam. The expanded object beam illuminates the sample to create the object wave front. After the object wave front is collected by a microscope objective, the object and reference wave fronts are joined by a beam splitter to interfere and create the hologram. Using the digitally recorded hologram, a computer acts as a digital lens and calculates a viewable image or information derived therefrom (e.g., cell mass).

Suitable DHM methods include, but are not limited to off-axis Fresnel DHM, Fourier DHM, image plane DHM, in-line DHM, Gabor DHM and phase-shifting digital holography.

Digital holograph microscopy of cells is described, for example, by Pan et al. (2012) *Optics Express*, 20(10): 11496-11505, 2012; Zhang et al. (2011) *Chinese Physics Letters*, 28(11): 114209; Kemper et al. (2006) *Biophotonics and New Therapy Frontiers*, 6191: 61910T-1-8; and Wang et al. (2013) *Computational and Mathematical Methods in Medicine* 2013, Article ID 715843.

EXAMPLES

The following examples are offered to illustrate, but not to limit the claimed invention.

Example 1

Quantifying Biomass Changes of Single CD8+ T Cells During Antigen Specific Cytotoxicity Existing approaches that quantify cytotoxic T cell responses rely on bulk or surrogate measurements which impede the direct identification of single activated T cells of interest. Single cell microscopy or flow cytometry methodologies typically rely on fluorescent labeling, which limits applicability to primary cells such as human derived T lymphocytes. Here, we introduce a quantitative method to track single T lymphocyte mediated cytotoxic events within a mixed population of cells using live cell interferometry (LCI), a label-free microscopy technique that maintains cell viability. LCI quantifies the mass distribution within individual cells by measuring the phase shift caused by the interaction of light with intracellular biomass. Using LCI, we imaged cytotoxic T cells killing cognate target cells. In addition to a characteristic target cell mass decrease of 20-60% over 1-4 h following attack by a T cell, there was a significant 2-3 fold increase in T cell mass relative to the mass of unresponsive T cells. Direct, label-free measurement of CD8+ T and target cell mass changes provides a kinetic, quantitative assessment of T cell activation and a relatively rapid approach to identify specific, activated patient-derived T cells for applications in cancer immunotherapy.

Materials and Methods

Cell Lines & PBMCs.

M202, M207, (Sondergaard et al. (2010) *J. Translational Med.* 8: 39) PC-3, PG13, and 293T cells (ATCC) were routinely maintained at 37° C. in 8% $CO_2$, using either DMEM or RPMI1640 Media supplemented with 5% FBS, 100 U/mL penicillin, 100 µg/mL streptomycin and 2 mmol/l-glutamine. HLA A2.1+ PBMCs derived from anonymized healthy donors were obtained from the Center for AIDS Research Virology Core Lab at UCLA and frozen following collection. Thawed PBMCs were revived in complete medium (CM) plus anti-CD3/2/28 beads for 4 d prior to retroviral infection. CM consisted of AIM-V media (Invitrogen, USA) supplemented with 25 mmol/L HEPES, 5.5×$10^{-5}$ mol/L [beta]-mercaptoethanol and 300 IU/mL IL-2. PBMCs were in culture for a total of 7-10 d prior to all imaging experiments. Cells were maintained in complete media on the LCI imaging platform.

Generation of MART1 Specific CD8+ T Cells.

F5 retrovirus was collected from PG13 cells modified to produce retroviral vector consisting of the F5 TCR with specificity toward the MART1 ELAGIGLTV peptide fragment, which is expressed by the M202 and M207 cell lines used in cytotoxicity experiments. Briefly, 293T cells were transfected with the packaging vector pCL-Eco and the MSCV-based retroviral vector RV-MSCV-FSMART1 TCR. Resulting supernatants were used to transduce the murine PG13 retrovirus packaging cell line for Gibbon ape leukemia virus (GaLV) envelope-pseudotype generation. PBMCs were infected with the retrovirus containing PG13 supernatant in the presence of Retronectin (Takara, Japan) according to the manufacturer's protocol. 48-72 h after infection the cells were stained with MART1 specific tetramer (Beckman Coulter, USA) and analyzed by flow cytometry (FACSCanto, BD Biosciences, USA). CD8+ T cells were isolated by negative enrichment (Stem Cell Technologies, USA) and the enrichment efficiency was verified by flow cytometry.

IFNg Measurement by Flow Cytometry.

To verify the functional specificity of DMFS transduced CD8+ T cells, a total of $1 \times 10^5$ T cells were co-cultured with $1 \times 10^5$ target cells (M202 or M207) in a 96-well flat plate with 200 µl of complete medium in a humidified incubator at 37° C. and 8% $CO_2$ for 18 h. The concentration of IFN-gamma in the supernatant was determined by flow cytometry using the Human IFNg FlowCytomix Simplex kit following the manufacturer's protocol (eBioscience, USA cat #BMS8228FF).

LCI Mass Measurements.

Target cells were plated onto 20 mm×20 mm silicon slides treated with a 0.01% solution of poly-l-lysine (Sigma) at a density of approximately $2.5 \times 10^4$ cells/$cm^2$ and allowed to grow in a cell culture incubator for 48 h prior to the start of imaging experiments. A silicon slide with attached target cells was placed into a custom-built, temperature and $CO_2$ controlled perfusion-based live cell imaging chamber and imaged for approximately 1.5 h before the addition of T cells. The T cell-target cell co-culture was imaged continuously for 18 h. 30 imaging locations were chosen based on suitable density of target cells on the silicon substrate and images collected approximately once every 3 to 4 min. Imaging was performed using a modified GT-X8 optical profiler (Bruker) at 20× magnification (numerical aperture 0.28) with a 0.55× demagnifying lens to increase field of view while preserving resolution. Interference fringes were generated using a Michelson-type interferometer consisting of a beam splitter, reference mirror and a reference fluid chamber which compensates for the optical path length through the sample chamber. Images were acquired using the phase-shifting interferometry (PSI) method and illumination from a 530 nm fiber-coupled LED (Thorlabs). Intensity images represent the average intensity of the image without the interference fringes necessary for Michelson phase imaging.

Phase Unwrapping.

To remove integer-wavelength phase ambiguities inherent in quantitative phase imaging (Ghiglia and Pritt, (1998) *Two-Dimensional Phase Unwrapping: Theory, Algorithms, and Software*: John Wiley & Sons.), we performed phase unwrapping using a custom script implemented in Matlab (Mathworks). First, we performed unwrapping based on Flynn's minimum discontinuity method (Id.). Next, a training dataset was constructed by manually applying single wavelength corrections to approximately 200 sub-images of the phase data, selected for the appearance of target and T cells of interest. This training dataset was used in a linear discriminant analysis (LDA) to identify pixels which lie on the boundary of phase-wrapped regions, based on 16 sets of image statistics, including the raw image itself, the computed intensity image, and the results of various edge-finding filters applied to the wrapped phase image. LDA was followed by genetic optimization to refine the LDA results and watershed algorithm thresholds used in determining the boundaries of phase-wrapped regions. Regions within the boundaries determined by the watershed algorithm applied to the final LDA result were shifted (corrected) by a phase shift of one wavelength and median filtered with a kernel size of 3.

Mass Tracking.

Single cell mass measurements were performed using a custom script implemented in Matlab (Mathworks). Briefly, phase-corrected images were Gaussian low pass-filtered before image segmentation based on Otsu thresholding. Finally, objects identified by image segmentation were tracked using the particle tracking code adapted for Matlab by Daniel Blair and Eric Dufresne, based on the particle tracking algorithm by Crocker and Grier (1996) *Science* 179: 12. Cell area was determined using a local adaptive threshold based on a 200 pixel neighborhood in the quantitative phase image.

Statistics.

Statistical analysis was performed using a two-tailed Welch's Student T test with unequal variances and sample sizes.

Results

LCI for Quantitative Imaging of T Cell Mediated Cytotoxicity

We developed a model system for analyzing cytotoxicity events by establishing the antigen specificity of healthy human donor CD8+ enriched lymphocytes against HLA matched target cell lines. Peripheral blood mononuclear cells (PBMCs) were transduced with an F5 anti-MART1 TCR, which is a high affinity TCR with specificity toward MART1 (Johnson et al. (2006) *J. Immunol.* 177: 6548-6559). Target cells expressing MART1 and antigen-defined CD8+ enriched T cells were co-cultured in a live-cell observation chamber on the LCI stage and imaged for a period of 18 h. (FIG. 2A). The observation chamber was temperature controlled and maintained pH by continuous perfusion of media at 8% $CO_2$. Following image collection, the light phase shift data was corrected for phase wrapping errors which are caused by the integer wavelength ambiguity inherent in quantitative phase imaging (Ghiglia and Pritt, (1998) *Two-Dimensional Phase Unwrapping: Theory, Algorithms, and Software*: John Wiley & Sons.). The result is a map of phase shifts across each cell that can be converted into a map of local dry mass density (FIG. 2B). The total dry mass of a cell is quantified as the sum of the local densities (Reed et al. (2011) *Biophys. J.* 101: 1025-1031; Ross (1967) *Phase contrast and interference microscopy for cell biologists*. London: Edward Arnold. xxi, 238 pp.; Mir et al. (2011) *Proc. Natl. Acad. Sci. USA,* 108: 13124-13129):

$$m = k \int \varphi \lambda \, dA, \quad (1)$$

where m is cell dry mass, $\varphi\lambda$ is the measured phase shift, k is the mass conversion factor, and A is projected area. The mass conversion factor (Barer (1952) *Nature* 169: 366-367; Mir et al. (2011) *Proc. Natl. Acad. Sci. USA,* 108: 13124-13129), which is a measure of the change in density per unit change in refractive index ($\Delta\rho/\Delta n$), is taken as k=5.56 pg/$\mu m^3$ (Ross (1967) *Phase contrast and interference microscopy for cell biologists*. London: Edward Arnold. xxi, 238 pp.). This parameter, k, is measured as a change in refractive index relative to the refractive index of water, Therefore, the cell mass measured in this manner is the cell dry mass, or the mass of everything within the cell other than water. With this equation, the measured dry mass of the activated T cell in (FIG. 2B) is 240 pg, the target cell mass is 840 pg and the unactivated T cells have an average dry mass of 65 pg.

Antigen-Specific T Cells and Maintenance of Viability on the Imaging Platform

Figure 3:
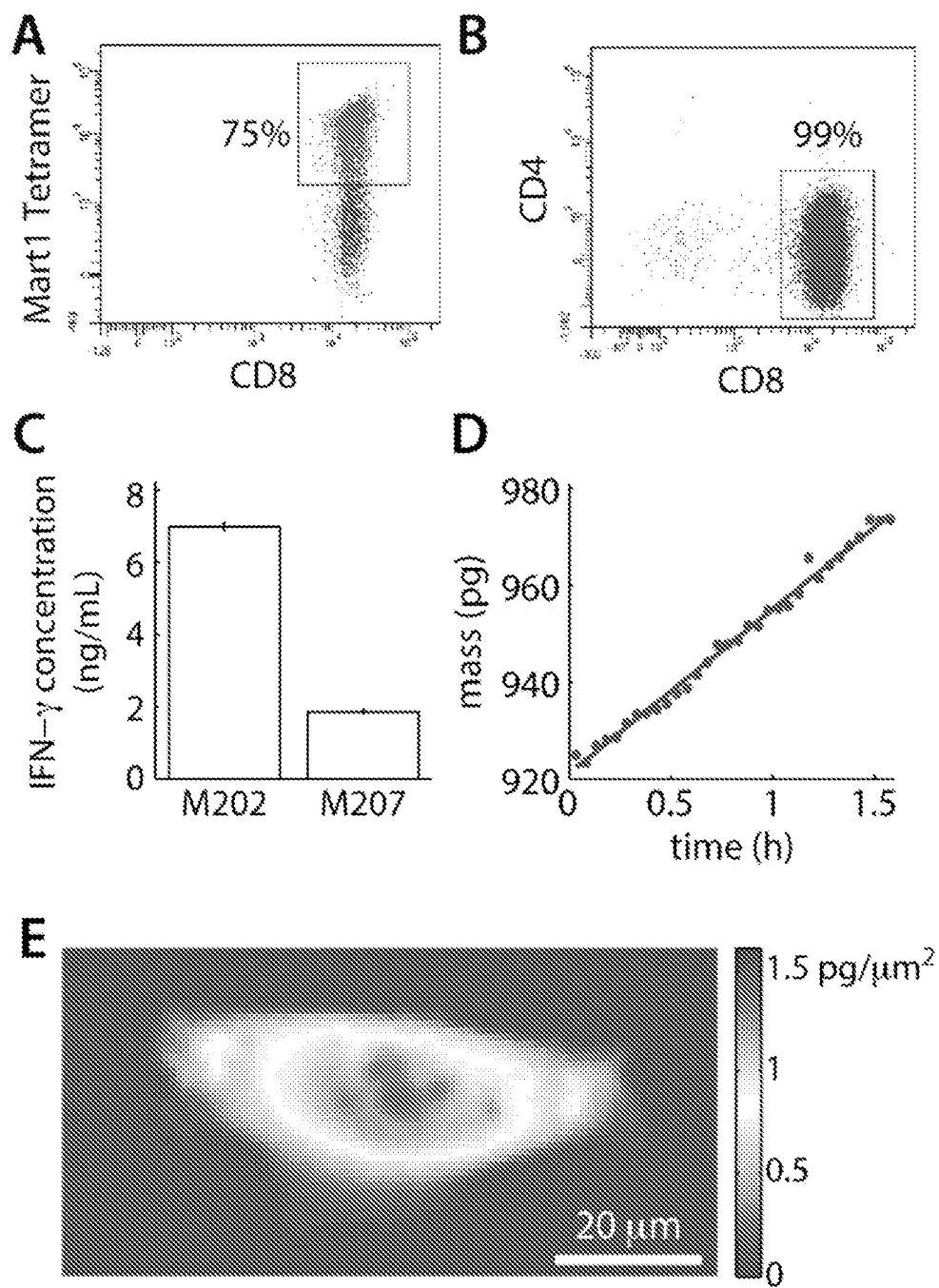
FIG. 3, panels A-E, illustrates transduction of CD8+ enriched PBMCs. (A) Flow cytometry data of transduced T cells showing typical transduction efficiency of donor PBMCs. (Panel B) Flow cytometry of CD8+ enriched population showing CD8+ T-cell enrichment efficiency. (Panel C) IFNg release assay validating F5-transduced, CD8+ enriched T cell activation following co-culture with HLA-matched MART1 expressing M202 cells. Negative control M207 cells express MART1, but are HLA-mismatched. (Panel D) Mass vs. time of the healthy M202 cell shown in (Panel E), demonstrating the viability of target cells on the interferometer stage.

To generate antigen-defined CTLs, we infected HLA A2.1+ healthy donor PBMCs with the F5 TCR by retroviral transduction and enriched for CD8+ cells by magnetic separation to remove magnetically labeled non-CD8+ cells (FIG. 3, panels A-B). Although CD8+ T cells have endogenous TCRs, ectopic expression of the F5 anti-MART1 TCR results in overexpression of the exogenous alpha and beta chains to allow for preferential pairing and surface expression. The majority of isolated cells were CD8+ with 75% expressing the F5 TCR on the surface, as determined by MART1 peptide tetramer stains prior to imaging. We measured interferon gamma (IFNg) accumulation in the supernatant following an 18 h co-culture period to verify that F5 redirected CD8+ T cells were specific for the cognate target cells. Results of a bead-based immunoassay analyzed by flow cytometry indicated a significant, 3.5-fold higher, IFNg release from F5 transduced CTLs upon co-culture with HLA-matched MART1+ M202 target cells as compared to co-culture with an HLA-mismatched control cell line (FIG. 3, panel C).

Figure 7:
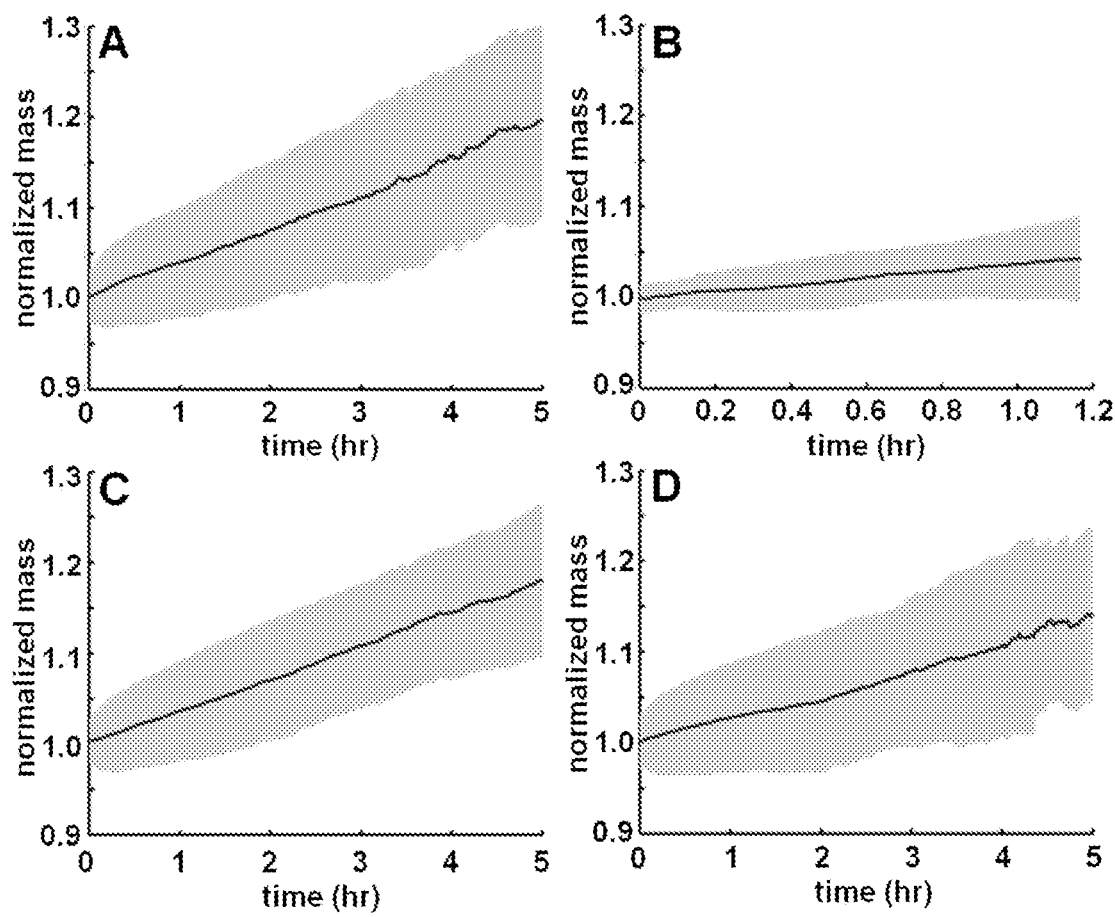
FIG. 7, panels A-D, shows averaged, normalized mass versus time plots for control target cell growth conditions showing robust growth on the LCI stage, and specificity of T cell mediated cytotoxicity. Panel A: Unaffected M202 cells (n=632) during treatment with F5 TCR transduced, CD8+ T cells. Panel B: M202 cells (n=117) prior to treatment with F5 TCR transduced, CD8+ T cells. Panel C: M202 cells (n=2058) treated with F5 TCR negative, CD8+ T cells. Panel D: Antigen-irrelevant, PC-3 prostate cancer cells (n=1006) treated with F5 TCR transduced, CD8+ T cells. Line shows mean normalized mass versus time (normalized relative to mass at first time point). Shaded region shows the mean +/−SD.
Figure 8:
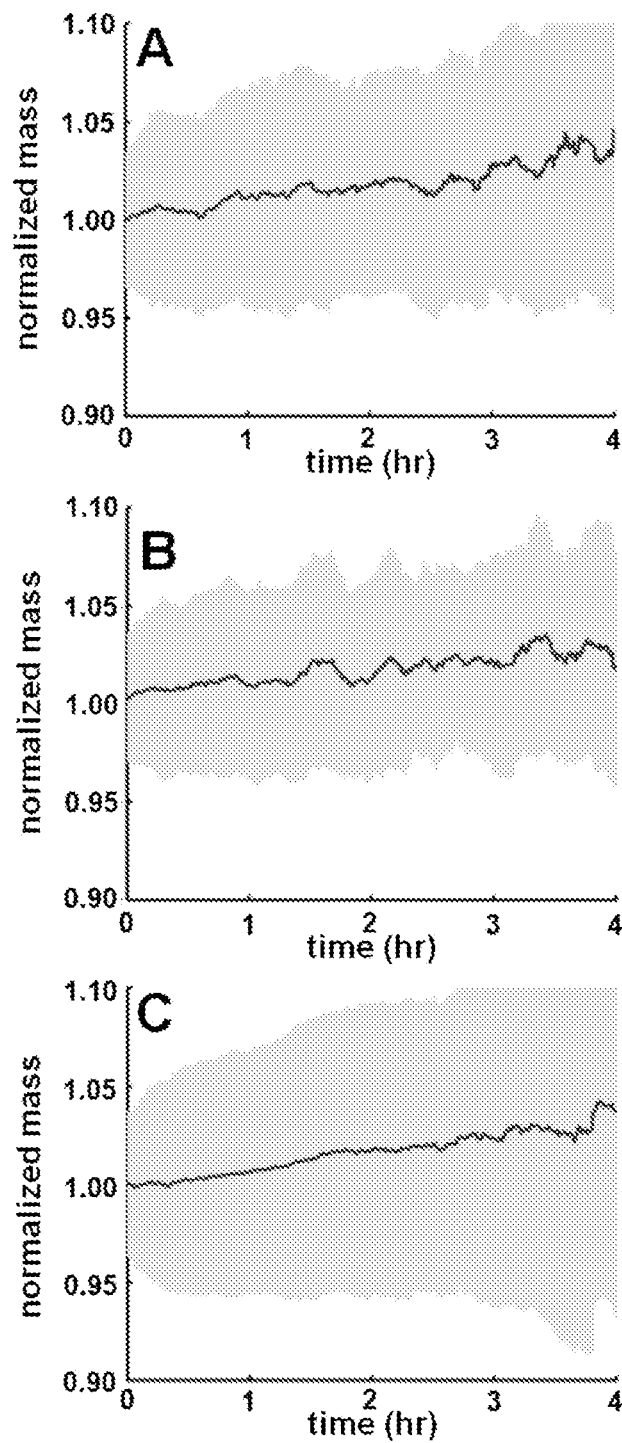
FIG. 8, panels A-C, shows averaged, normalized mass versus time for unresponsive T cells, showing steady growth on the LCI stage. Panel A: Unresponsive F5 TCR transduced CD8+ T cells (n=101) plated with M202 target cells. Panel B: Untransduced CD8+ T cells (n=146) plated with M202 target cells. Panel C: F5 TCR transduced CD8+ T cells (n=950) plated with antigen-irrelevant, PC-3 prostate cancer target cells.

Target cells were imaged in standard culture media for 1.5 h prior to the start of each experiment to confirm the live cell culture imaging platform maintains viability of target cells in the absence of CTLs. M202 target cells showed a positive mass accumulation rate, indicating a healthy population and the maintenance of cell viability. (FIG. 3, panels D-E; FIG. 7, panel B). Control experiments demonstrated maintenance of both T and target cell viability during extended imaging periods (FIGS. 7 and 8).

Mass Decrease of Killed Target Cells

After 1.5 h of target cell control measurements, F5 MART1 reactive CTLs (FIG. 3, panels A-B) were added to the live cell imaging chamber and imaged continuously for 18 h. This experiment duration is similar to the time period typically required for measurement of T cell activity by ELISPOT (Hobeika et al. (2005) *J. Immunother.* 28: 63-72). Single CTLs killing individual target cells are identified through qualitative analysis of the intensity image data as a change in appearance of the target cell following prolonged contact with a CTL (FIG. 4, panels A-D). Cytotoxic events are detectable despite the presence of nonspecific or unresponsive T cells within the broader population. LCI provides quantitative maps of the mass distribution within target cells during T cell mediated cytotoxic events (FIG. 4, panels E-H). These mass distributions from successive image frames can be integrated to yield measurements of target cell mass over time (Equation 1 and FIG. 4, panel I). Individual cytotoxic events due to recognition of CTLs are confirmed by a characteristic decrease in target cell mass following prolonged contact (30 m to 2 h) with a corresponding CTL (FIG. 4, panel I and movie, images of which are shown in FIGS. 6A-6F).

Figure 9:
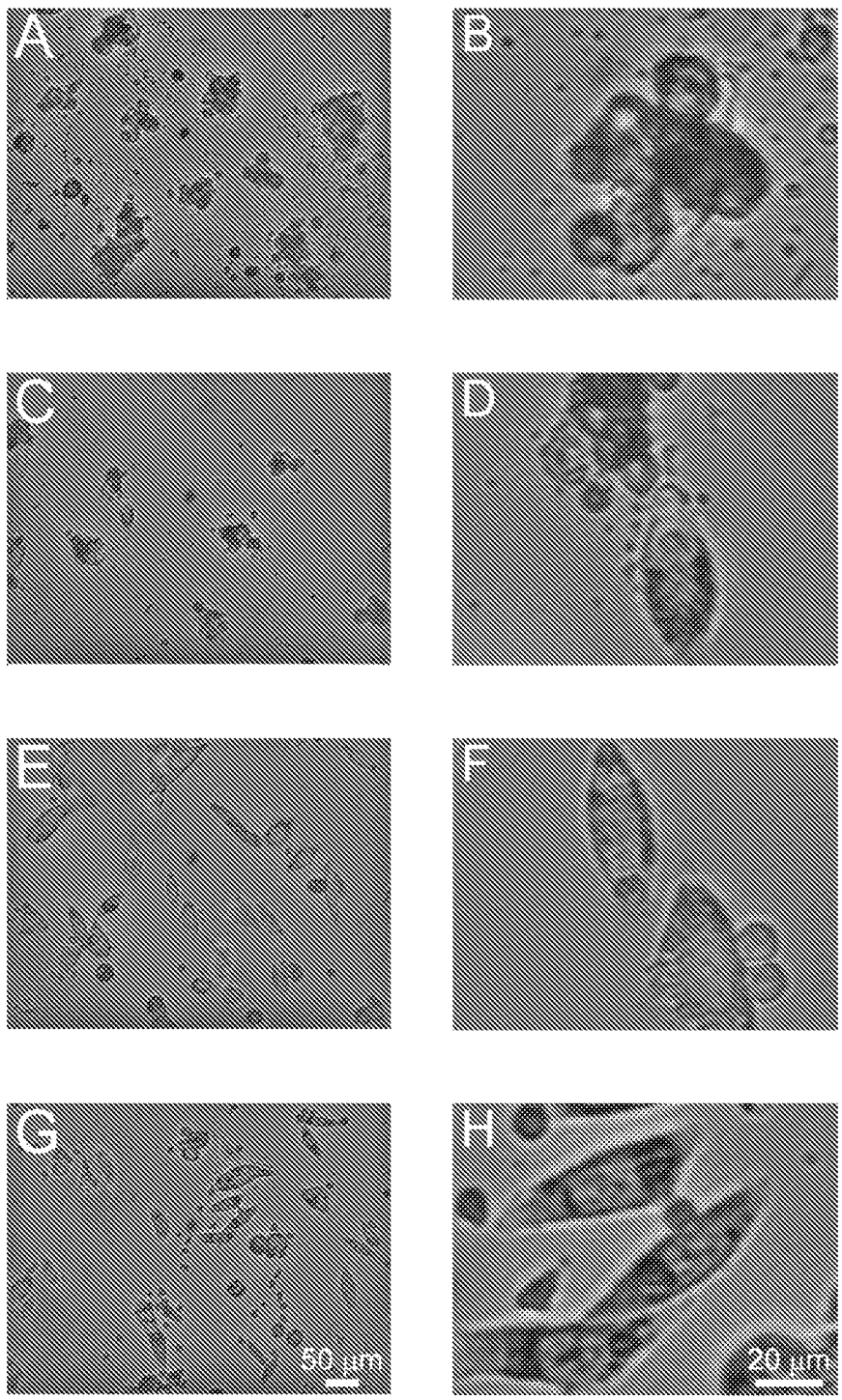
FIG. 9, panels A-H, shows intensity images of cells on the interferometer stage after 18 h of imaging showing typical target cell conditions. Left column shows the full image frame, the right column shows a subset of the full image frame. Panels A-(D: M202 target cells plated with F5 TCR transduced, CD8+ T cells showing nearly complete death of target cells. For comparison, (panels A and B) show the same field of view as in FIG. 3, panels A-F. Panels C and D show a single living cell. Panels E and F: M202 target cells plated with untransduced CD8+ T cells showing viability on the stage after 18 h of imaging and cognate TCR requirement for T cell mediated cytotoxicity. Panels G and H: Antigen-irrelevant PC-3 prostate cancer target cells plated with F5 TCR transduced CD8+ T cells showing the specificity of the F5 TCR.

Target cell mass decreased by 20 to 60% over a period of 1-4 h when successfully attacked by a CTL, as compared to an increase in total target cell mass of 15% over 4 h when not killed by CTLs (FIG. 4, panels I-J). Despite contact between T cells and target cells, there was no response in control experiments using HLA mismatched, antigen irrelevant target cells (lacking MART1) or non-specific T cells (FIG. 4, panels K-M; FIG. 7, panels C-D, and 9, panels C-D). This indicates that target cell death was due to the presence of antigen-specific CTLs and that the rate and extent of target cell mass decrease due to T cell mediated cytotoxicity is directly quantifiable using LCI. T cell mediated cytotoxicity is evident within the first 30 min and confirmed within the first 2-4 h following the addition of CTLs, indicating the speed of the LCI approach in measuring T cell mediated cytotoxicity (movie FIGS. 6A-6F). An estimated 95% of target cells were dead by 18 h after the addition of CTLs, while greater than 95% of control target cells appeared healthy at 18 h (FIG. 4, panels K-L; FIG. 9).

Mass Increase of Activated CTLs

Figure 5:
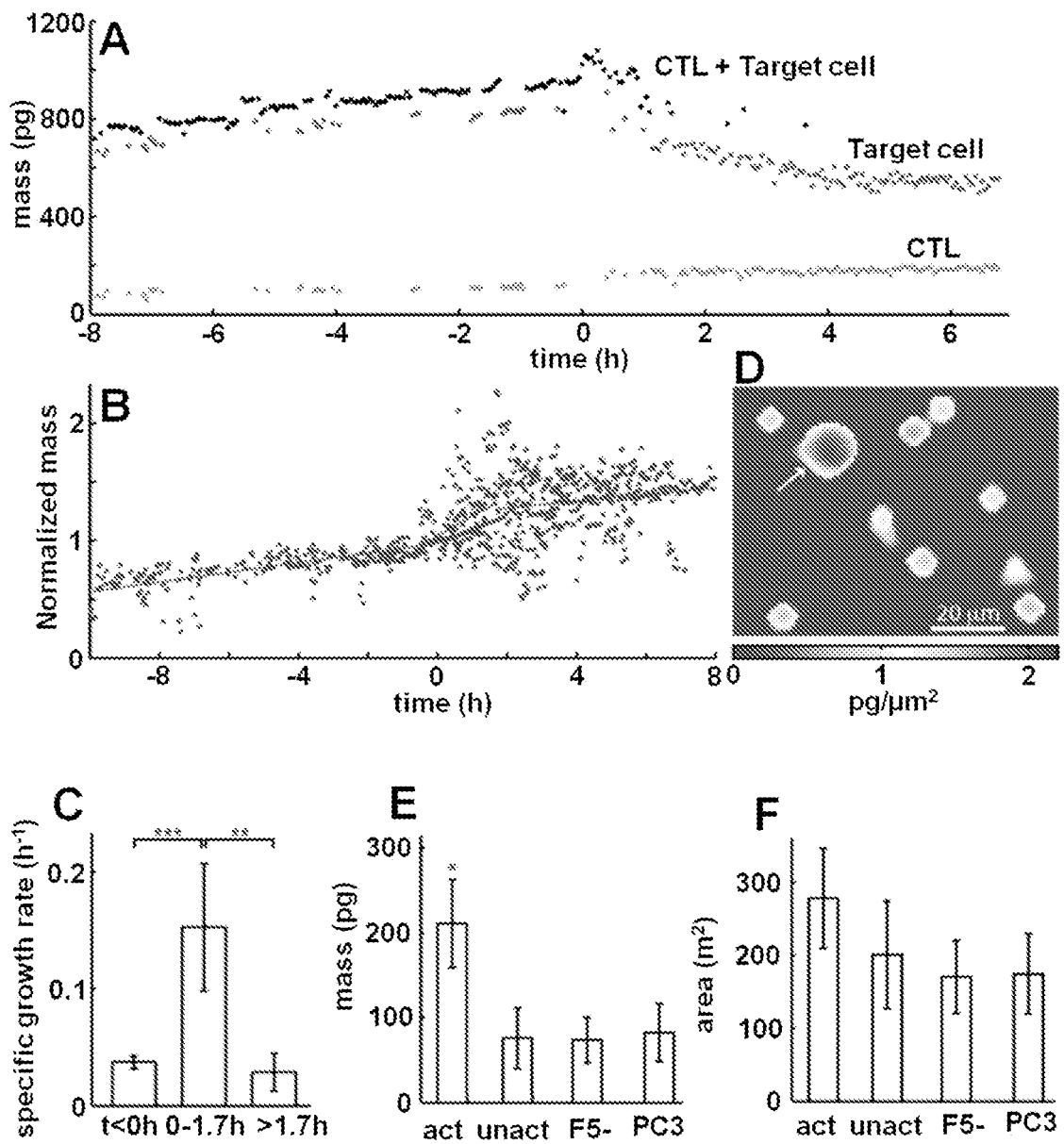
FIG. 5, panels A-F, illustrate LCI measurement of CTL mass and mass accumulation rate during T cell mediated cytotoxicity. Panel A: Mass versus time of an activated CTL and corresponding target cell. t=0 h is the point at which the target cell detaches from the substrate at the beginning of cell death. CTL+target cell refers to total mass of both cells in frames where they could not be measured separately. Panel B: Normalized mass versus time of 10 CTL-mediated cytotoxicity events. CTL mass is normalized relative to the mass at the time of target cell morphology change, which is used as the t=0 h point for all traces. Gray lines show best fit lines used for determining mass accumulation rates. Panel C: Average mass accumulation rate of CTLs before a cytotoxic event, during the first 100 minutes of a cytotoxic event, and after the first 100 minutes of a cytotoxic event demonstrating an approximately 4-fold increase in mass accumulation during the first 100 minutes of a cytotoxic event. Panel D: LCI image of 9 unresponsive and 1 cytotoxic T cell illustrating an approximately 3-fold difference in mass. The white arrow indicates the activated T cell, as determined by tracking this cell after persistent contact with target cell and subsequent target cell death. Panel E: The average mass of 116 activated CTLs is approximately 2.8-fold greater than the average mass of unresponsive controls. Panel F: Average area of activated CTLs is only approximately 1.4-fold greater than non-activated controls and not significant at the 95% confidence level, illustrating the utility of LCI mass measurements for determining CTL activation. Error bars in C show 95% confidence intervals. Error bars in E and F show +/−SD. *$p<0.05$, $p<0.01$, *$p<10^{-3}$. act=activated/cytotoxic, 116 cells, n=3 experiments. unact=unactivated/unresponsive, 359 cells, n=3 experiments. F5−=untransduced, F5-negative control experiment, 530 cells, n=2 experiments. PC3=PC3 cell, HLA-mismatched irrelevant antigen control, 3015 cells, n=3 experiments.
Figure 6A:
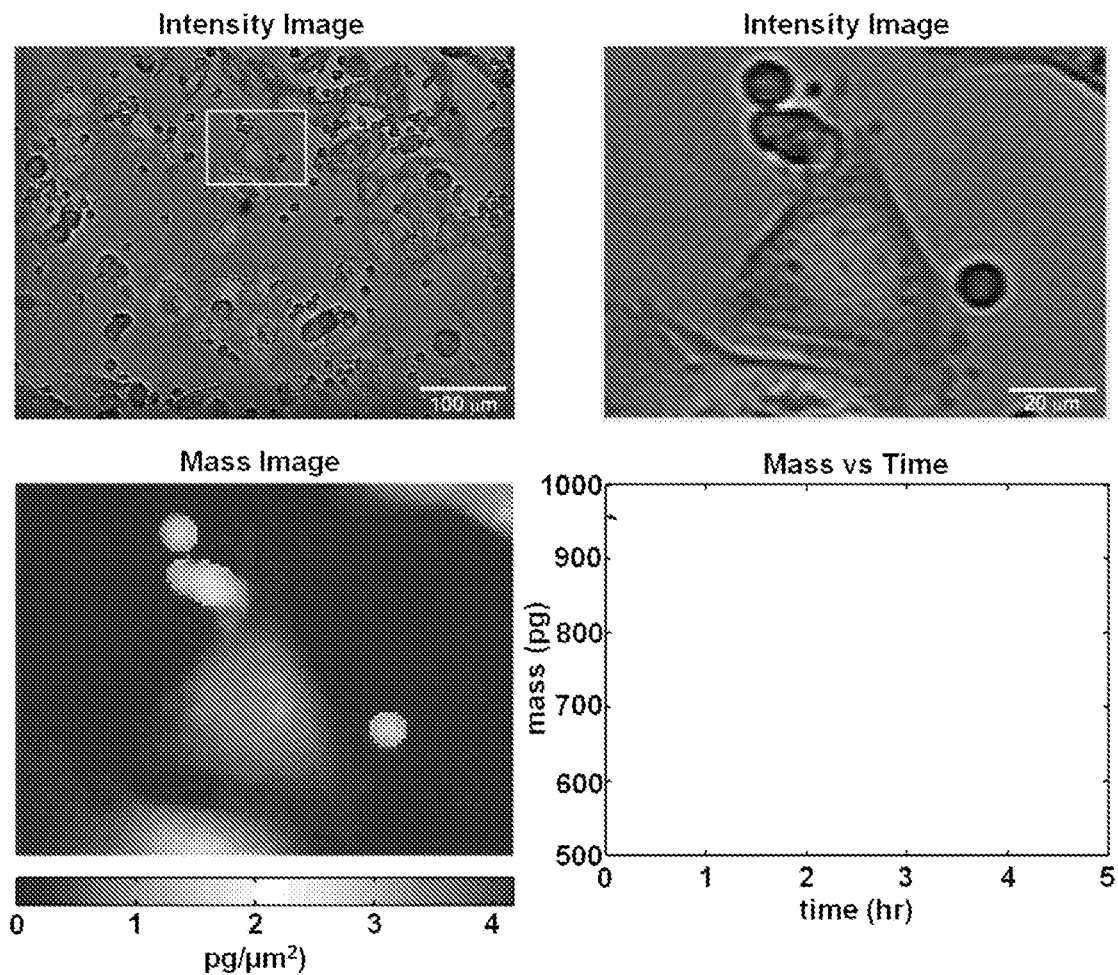
FIGS. 6A-6F show images from a four panel video showing intensity images, mass distribution images, and mass vs. time of a target M202 cell being killed by a cytotoxic T cell (CD8+, F5 TCR transduced) over the course of 5 hours of observation by LCI.
Figure 6B:
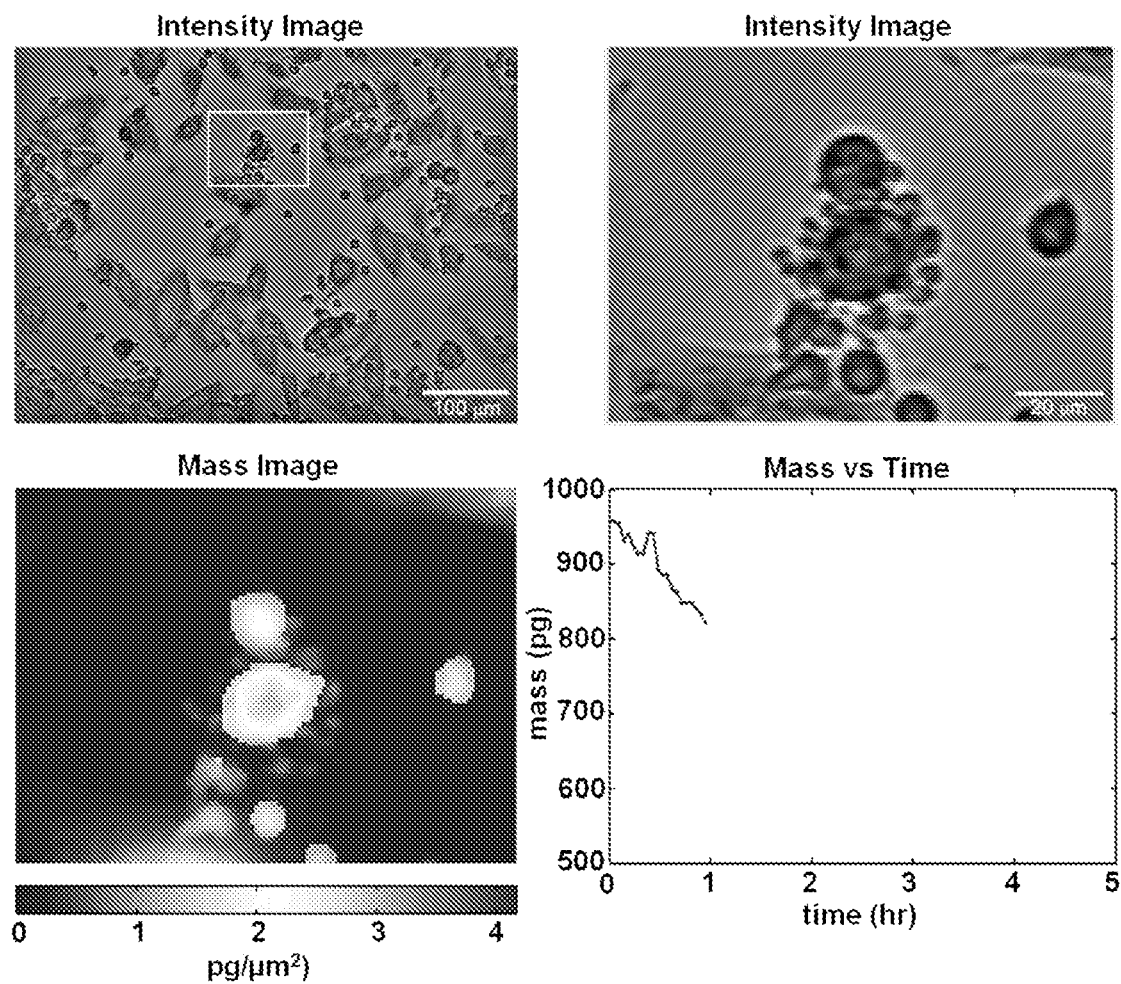
Figure 6C:
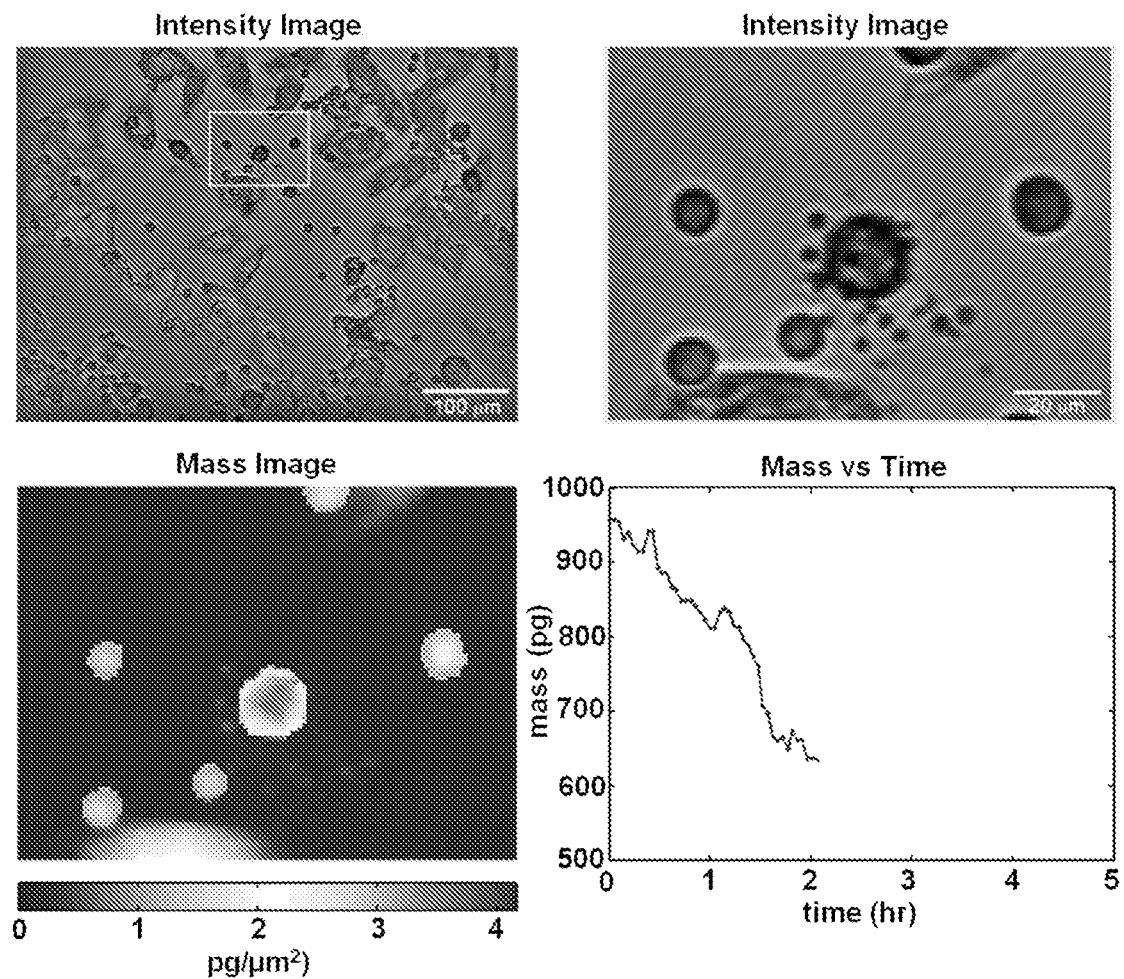
Figure 6D:
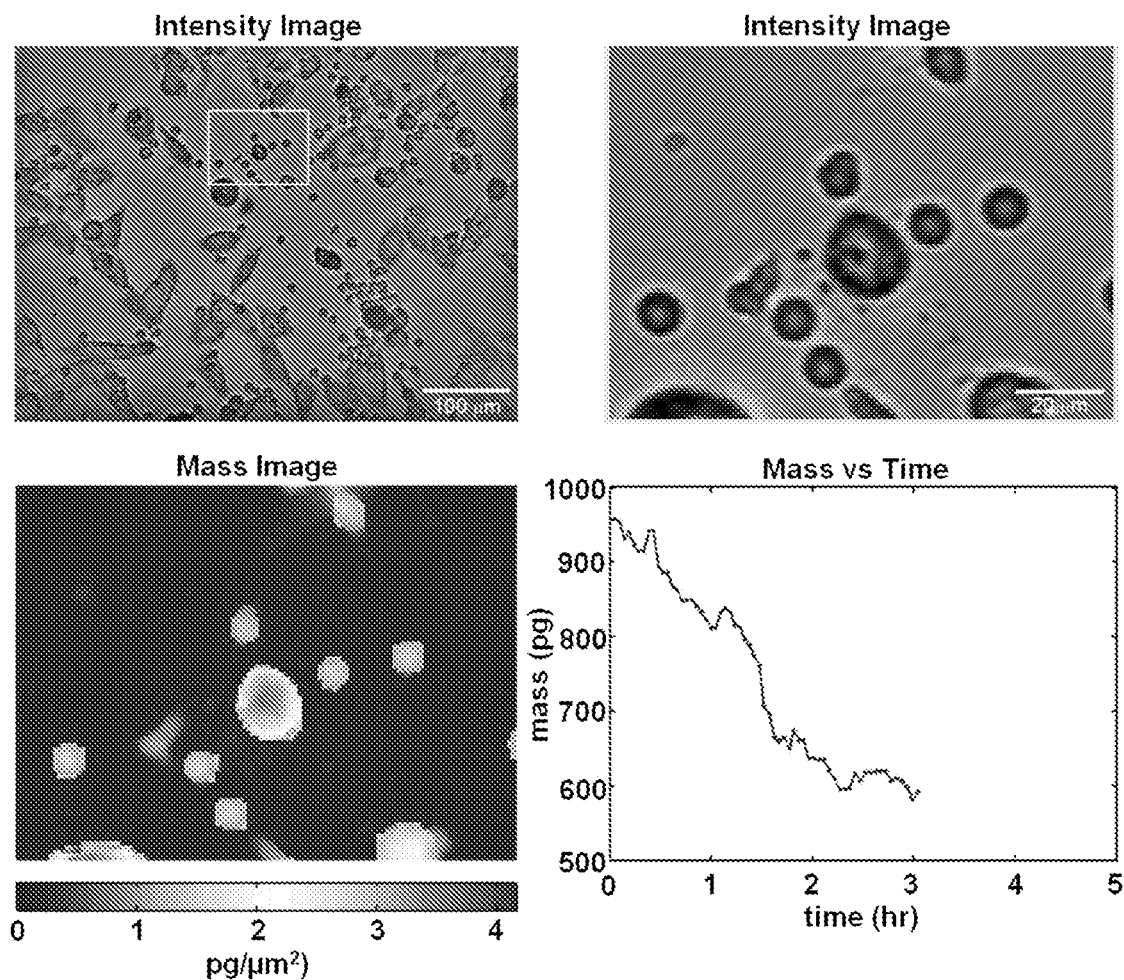
Figure 6E:
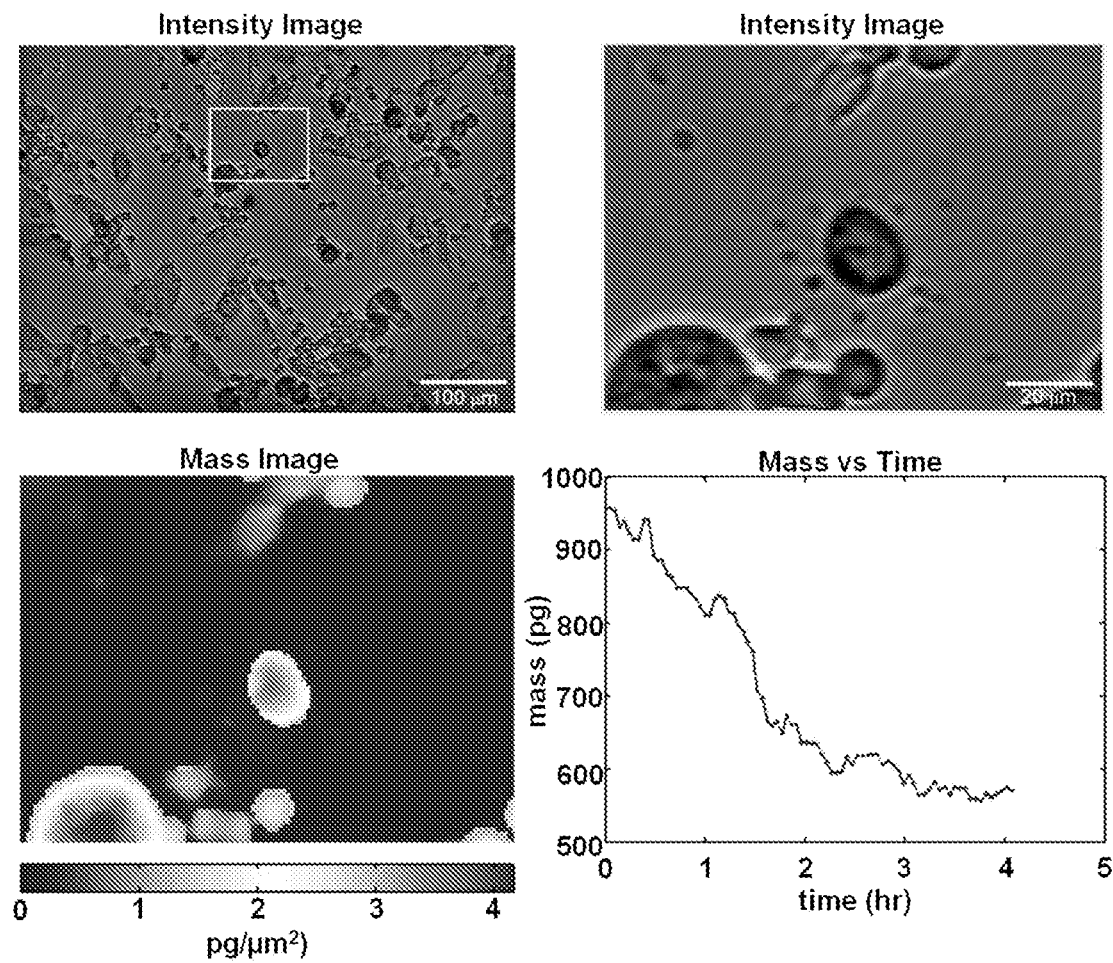
Figure 6F:
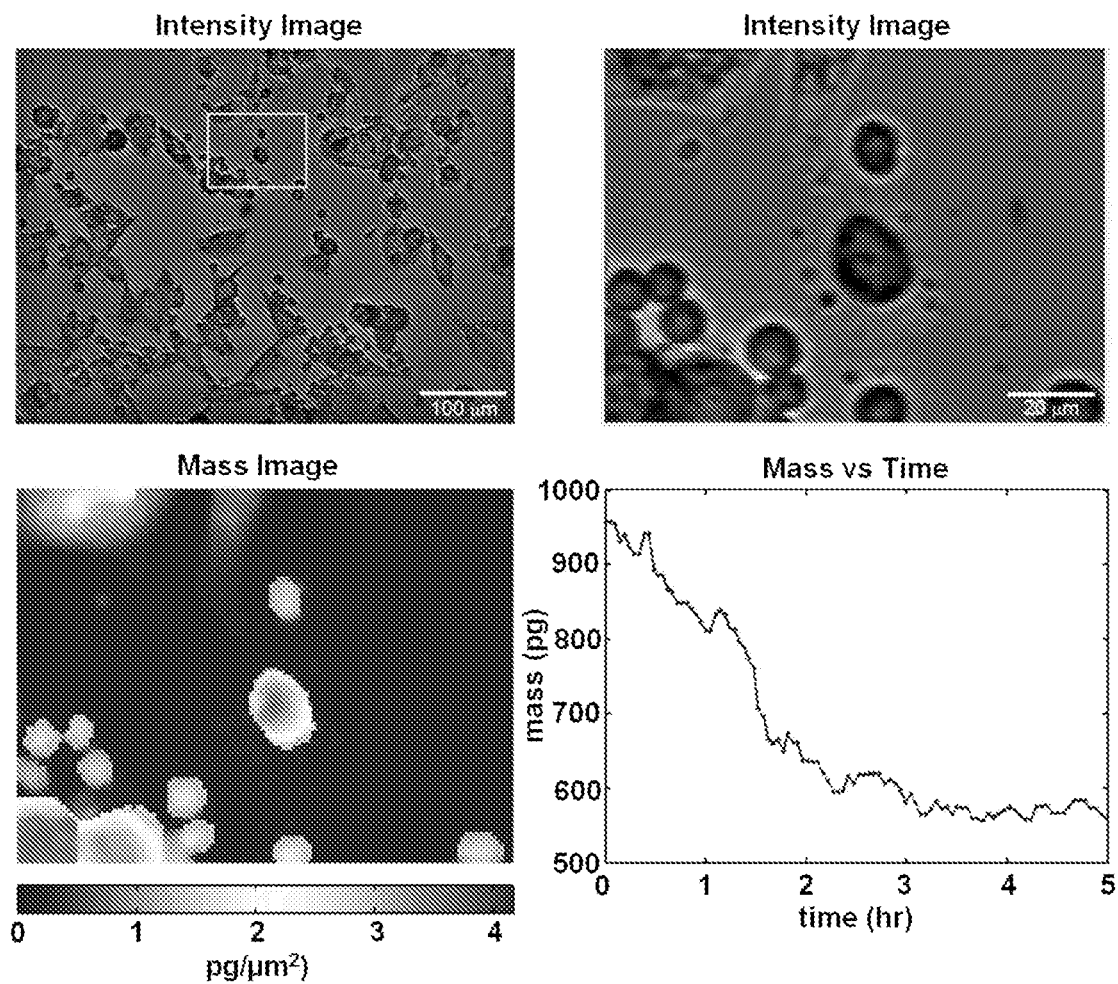
Figure 10:
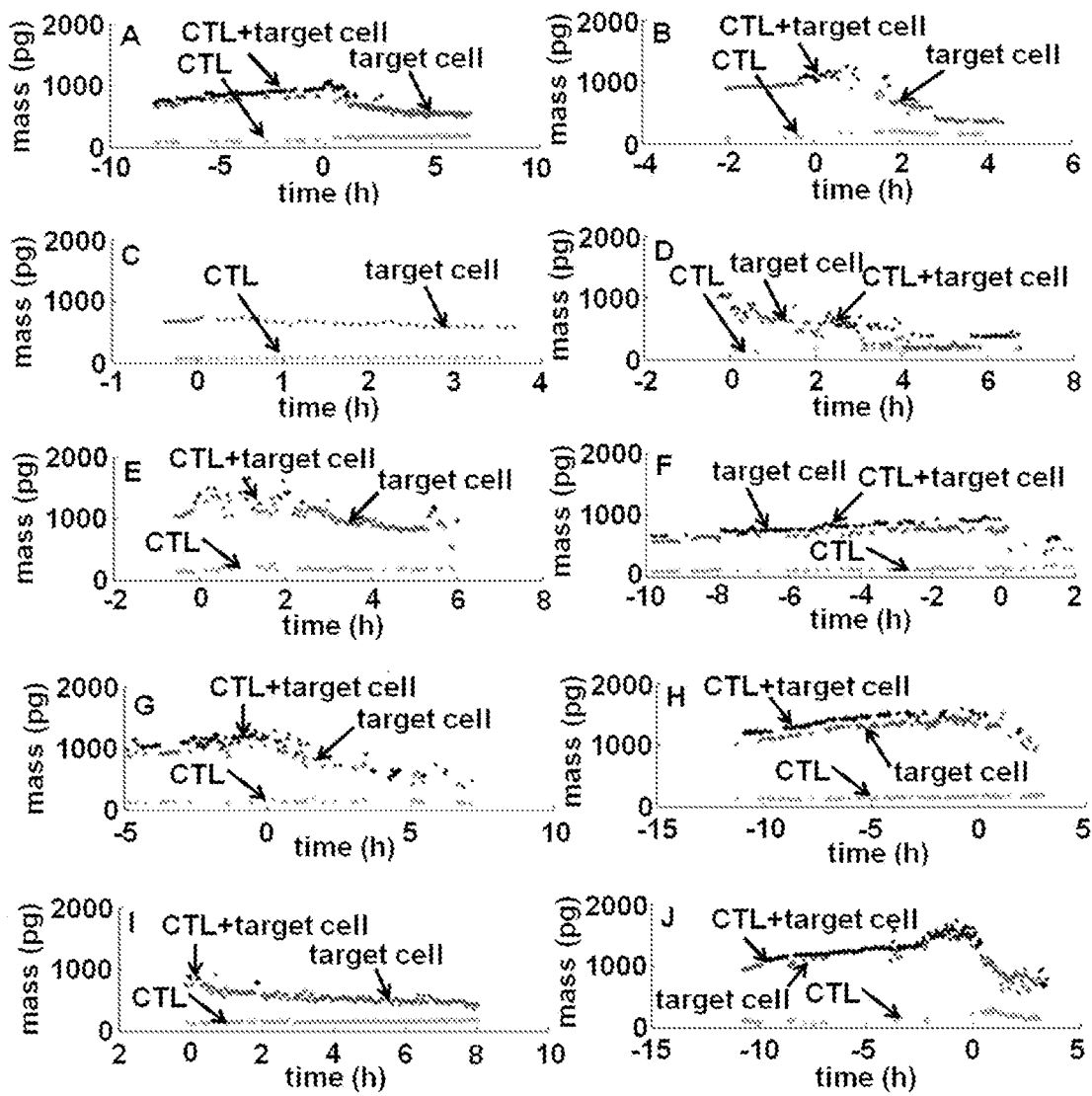
FIG. 10, panels A-J, show mass versus time plots for CTLs and corresponding target cells, as in FIG. 5, panel A. t=0 h is the point at which the target cell detaches from the substrate at the beginning of cell death. CTL+target cell refers to total mass of both cells in frames where they could not be measured individually, typically due to overlap between the CTL and target cell.

In parallel with the decrease in target cell mass, individual activated CTLs increased in overall size by the end of a cytotoxic event (FIG. 5). Individual CTL and target cell masses can be tracked through the duration of their interactions (FIG. 5, panel A; FIG. 10). CTL mass versus time data for 10 such events is summarized in FIG. 5, panel B, with CTL mass normalized relative to the mass when the target cell dramatically changed morphology ("balled-up") at the start of a death event, which is defined as t=0 h. In a typical trace, the target cell initially shows an increase in mass consistent with the growth rate of a healthy cell (FIG. 4, panel M). During this period (t<0 h), CTLs show a relatively slow growth rate (FIG. 5, panel C). Then, the target cell "balls-up" and detaches from the substrate, immediately prior to a very rapid loss of mass over the first 1-2 hours. During this initial period (approximately 100 min), the T cell mass accumulation rate increases significantly (FIG. 5, panel C). As the target cell loses mass and the central cell body condenses over the next 2-5 hours, the T cell continues to increase in mass, at a slower rate than during the initial period (FIG. 5, panel C).

Figure 11A:
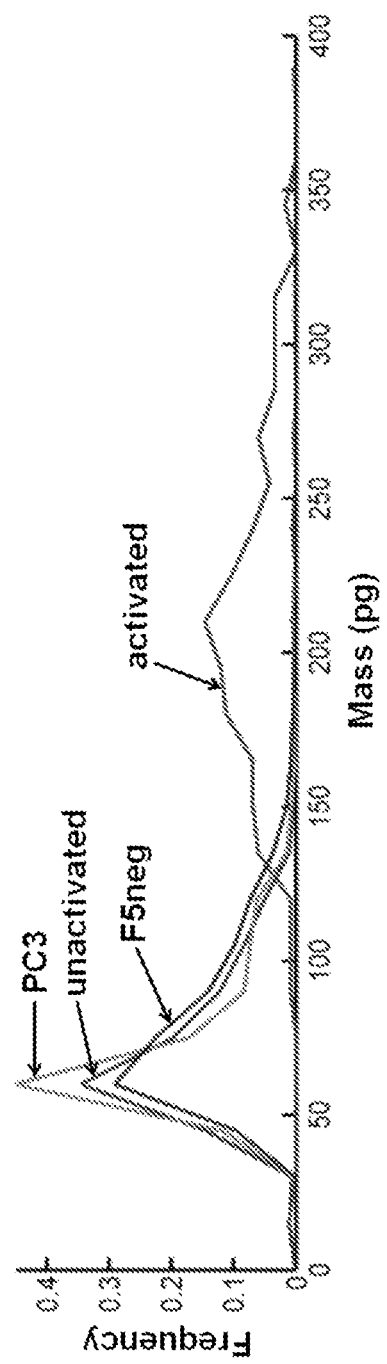
FIG. 11A mass and FIG. 11B area histograms for activated and unresponsive T cells, relative to control experiments. Activated=activated/cytotoxic F5 TCR transduced T cells, 116 cells, n=3 experiments. Unactivated=unactivated/unresponsive F5 TCR transduced T cells, 359 cells, n=3 experiments. F5neg=untransduced F5 TCR negative T cells plated with M202 target cells, 530 T cells, n=2 experiments. PC3=F5 TCR transduced T cells plated with HLA-mismatched antigen irrelevant PC-3 prostate cancer cells, 3,015 T cells, n=3 experiments
Figure 11B:
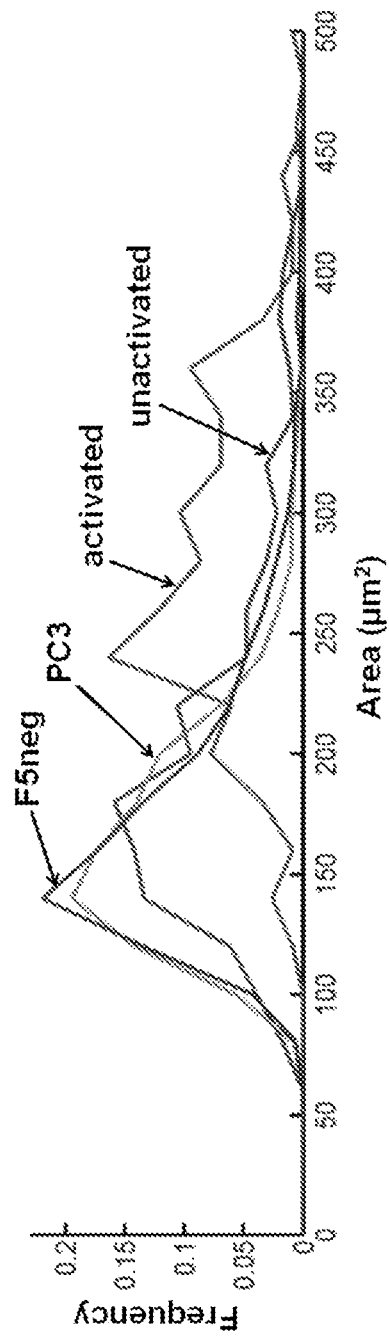

This change in mass accumulation rate resulted in a significant 2 to 4-fold higher cellular mass than surrounding unresponsive T cells (FIG. 5, panel D). The total cellular mass of 116 CTLs at the end-point of each cytotoxic event was compared to the mass of 3,900 control T cells that did not kill targets during the course of the experiment. On average, the CTLs had a 2.8-fold higher mass as compared to their non-specific or unresponsive counterparts (FIG. 5, panel E; FIG. 11, panel A). This mass increase persisted for up to 4 h, a duration that is limited by the average period of observation prior to the activated T cell being washed away due to continuous media perfusion through the observation chamber.

The two-dimensional (2D) area of responsive versus unresponsive T cells was calculated to determine whether there was a significant difference relating to overall size. The observed 1.4-fold increase in 2D area was smaller than the 2.8-fold difference in total cell mass and did not achieve statistical significance at the $p<0.05$ level compared to controls (FIG. 5, panel F; FIG. 11, panel B). These results show that the mass change of CD8+ T cells is a more robust indicator for activity than the change in cell area. Additionally, for spherical T cells, the observed 1.4-fold increase in mass corresponds to a 1.7-fold increase in volume, which is substantially lower than the observed 2.8-fold increase in mass. These results, therefore, suggest that there is also an increase in T cell density during activation, although density quantification is not possible with the present configuration of LCI measurements.

Discussion

LCI provides a quantitative label-free cytotoxicity assay through sensitive biomass measurements of single effector T cells and their affected target cells during cytotoxic events (FIG. 2). The mass of killed target cells can be tracked over time to confirm a 20 to 60% decrease in mass over 1 to 4 h, consistent with a cytotoxic insult (FIG. 4). We found a significant 2.8-fold average increase in total mass of effector T cells after recognition and killing of cognate target cells (FIG. 5). The change of mass of T cells was found to be a more significant indicator of T cell activation state than measurements of 2D changes in area alone.

The mass increase we observed in activated CTLs is likely accompanied by an increase in biosynthesis driven by metabolic changes. It has been demonstrated that T cells use glucose and glutamine as their primary energy sources. Activated lymphocytes generate energy to meet protein synthesis demands by significantly increasing glucose, amino acid and fatty acid uptake from the extracellular environment (Fox et al. (2005) *Nat. Rev. Immunol.* 5: 844-852). Glucose deprivation studies have shown that activated T cells require glucose for proliferation and survival even in the presence of adequate levels of glutamine (Michalek and Rathmell (2010) *Immunol. Rev.* 236: 190-202). TCR signaling plays a critical role in regulating the transcription of the glucose transporter Glut1, enabling enhanced glucose uptake with activation (Maciver et al. (2008) *J. Leukoc. Biol.* 84: 949-957). Studies have shown that TCR agonists such as anti-CD3 antibodies or compounds that cause cross-linking of CD3 proteins result in a rapid and maximal induction of Glut1 expression (Michalek and Rathmell (2010) *Immunol. Rev.* 236: 190-202; Maciver et al. (2008) *J. Leukoc. Biol.* 84: 949-957).

A potential application of the LCI technique presented here is for the identification and isolation of single and potentially rare CTLs. A growing body of work has focused on the identification of tumor infiltrating T lymphocytes (TILs) bearing TCR recognition of autologous tumor cells (Rosenberg et al. (2008) *Nat. Rev. Cancer,* 8: 299-308; Cheever et al. (2009) *Clin. Cancer Res.* 15: 5323-5337). Recent studies have indicated that these CTLs occur at relatively low frequencies, making it difficult to employ bulk or surrogate cytotoxicity assays to confirm their existence and isolation from a mixed population (Elkord et al. (2006) *Clin. Immunol.* 120: 91-98; Whiteside (2004) *Dev. Biol.* (Basel) 116: 219-228; discussion 229-236). The LCI approach uses the cytotoxic interaction between CTLs and target cells as a natural amplifier of the underlying peptide-MHC-TCR recognition event which avoids false positives due to nonspecific binding. The LCI imaging platform is fundamentally compatible with a segmented culture system that will allow for isolation of rare cells that may be lost in the current open perfusion cell culture system. LCI may therefore provide a viable alternative for the identification and isolation of rare effector T cells killing autologous tumor cells or HLA-matched cancer cell lines.

T cells against cancer-associated antigens are generally anticipated to bear lower affinity TCRs if they are raised against a self-antigen and presumably escaped thymic selection and tolerance induction (Wooldridge et al. (2009) *Immunology* 126: 147-164). The affinity between the TCR and peptide-MHC is considered to play a crucial role in the outcome of T cell stimulation (Stone et al. (2009) *Immunology* 126: 165-176). The classic method to assess TCR-peptide-MHC affinity entails the measurement of on and off-rates using surface plasmon resonance. The surface bound peptide-MHC-TCR interaction does not accurately mimic the multiple receptor-mediated interactions that occur during recognition of a target cell by a CTL. Evidence suggests that these measurements provide limited information regarding lymphocyte effector function (Stone et al. (2009) *Immunology* 126: 165-176; Edwards and Evavold (2011) *Immunol. Res.* 50: 39-48). In a transfection system, TCRs engineered with higher affinity for cognate peptide-MHC ligands compared to their wild type counterpart exhibited increased CTL activity (Edwards and Evavold (2011) *Immunol. Res.* 50: 39-48). An affinity model suggests that activation of T cells is related to the number of receptors engaged. Higher affinity interactions require less TCR-peptide-MHC engagements to activate a T cell into a cytotoxic state (Tian et. al.. (2007) *J. Immunol.* 179: 2952-2960). It is conceivable that higher affinity TCR-peptide-MHC interactions drive a more rapid response than their lower affinity counterpart, and the LCI approach may also potentially discriminate between these interactions.

Acknowledgements

We thank Dr. Ribas' laboratory (UCLA) for supplying cell lines and Dian Huang (UCLA) for her assistance with data analysis. This work would not be possible without the UCLA Center for AIDS Research Virology Core Lab and their donors who supply healthy HLA A2.1+ PBMCs.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of identifying and isolating individual CD8+ T cells bearing a T cell receptor that responds to a specific antigen, said method comprising:
    providing a substrate bearing a plurality of target cells that present said specific antigen;
    contacting said target cells on said substrate with CD8+ T cells;
    performing quantitative phase imaging microscopy where said phase imaging microscopy comprises detecting a phase shift in light passing through said CD8+ T cells to identify individual CD8+ T cells that show an increase in mass in response to contacting said target cells presenting said specific antigen; and
    selecting, and culturing or storing the individual CD8+ T cells that show an increase in mass to provide isolated T cells bearing a T cell receptor that responds to said specific antigen.

2. The method of claim 1, wherein said quantitative phase imaging microscopy comprises a method selected from the group consisting of live cell interferometry (LCI), digital holography, and lateral shearing interferometry.

3. The method of claim 2, wherein said quantitative phase imaging microscopy comprises live cell interferometry utilizing an interference microscope.

4. The method of claim 3, further comprising cloning T cell receptors from CD8+ T cells that are selected and cultured or stored.

5. The method of claim 1, wherein said target cells:
    are in static media; and/or
    are disposed in a microchannel; or
    are disposed in microwells on a substrate.

6. The method of claim 5, wherein said target cells are disposed in microwells on a substrate that comprises at least 10 microwells, and/or that comprises at least 100 microwells, and/or that comprise at least 1000 microwells.

7. The method of claim 6, wherein said T cell are introduced into said microwells.

8. The method of claim 7, wherein the microwells contain on average about 1 T cell per microwell.

9. The method of claim 6, wherein said microwells are fabricated from a polymer or etched into a silicon substrate.

10. The method of claim 1, wherein said substrate is reflective.

11. The method of claim 1, wherein said using label-free optical imaging comprises detecting a phase shift in light passing through said cell(s) caused by the change in T-cell mass and/or target cell mass.

12. The method of claim 11, wherein said label-free optical imaging comprises quantitative phase imaging microscopy.

13. The method of claim 3, wherein said live cell interferometry comprises:
    providing said substrate in an observation chamber of an interference microscope adapted to measure a fractional phase shift between a test beam of light and a reference beam of light;
    exposing the cell to a test beam of light at an illumination wavelength;
    measuring the fractional phase shift between the test beam of light propagating through the cell and the reference beam of light; and
    using said fractional phase shift or a parameter derived therefrom as a measure of the increase in mass of the T cell and/or the decrease in mass of the target cell.

14. The method of claim 13, wherein said fractional phase shift is integrated across substantially the entire projected area of the cell whose mass change is being determined.

15. The method of claim 13, wherein said measure of the increase in mass of the T cell and/or the decrease in mass of the target cell is calculated as parameter m:

$$m \propto \int \varphi \lambda dA,$$

where $\varphi$ is the measured fractional phase shift, $\lambda$ is the illumination wavelength, and integration is performed across entire cell area, A.

16. The method of claim 13, wherein the method is performed using a live cell interferometry system comprising:
    a detector operatively coupled to a microscope;
    a sample chamber (perfusion imaging chamber) containing said substrate comprising a plurality of microwells; and
    an interferometer comprising a beam splitter, a reference mirror, and a reference fluid chamber that compensates for the optical path length through the sample chamber.

17. The method of claim 1, wherein the mass of the cell(s) is observed a plurality of times so as to observe how the mass of the cell(s) changes over a period of time.

18. The method of claim 1, wherein said target cells comprise cancer cells, or cancer stem cells.

19. The method of claim 1, wherein said target cells comprise cells infected with a pathogen, or cells transfected with a construct that expresses a heterologous protein or peptide.

20. The method of claim 18, wherein said selecting, and culturing or storing the CD8+ T cells comprises selecting and/or storing cytotoxic T lymphocytes (CTLs).

* * * * *